US006451618B2

(12) United States Patent
Hanas

(10) Patent No.: US 6,451,618 B2
(45) Date of Patent: *Sep. 17, 2002

(54) TEST FOR DETECTING SUBSTANCES WHICH ALTER THE CONFORMATIONAL STRUCTURE OF ZINC FINGERS

(75) Inventor: Jay S. Hanas, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,201

(22) Filed: Feb. 2, 2001

Related U.S. Application Data

(63) Continuation of application No. 09/034,705, filed on Mar. 4, 1998, now Pat. No. 6,235,538.
(60) Provisional application No. 60/039,873, filed on Mar. 5, 1997.

(51) Int. Cl.[7] ................... G01N 33/566; G01N 33/533; G01N 33/535
(52) U.S. Cl. .................... 436/501; 435/6; 435/7.92; 436/546; 436/815
(58) Field of Search ................. 436/501, 546, 436/815; 435/6, 7.92

(56) References Cited

U.S. PATENT DOCUMENTS

| | | |
|---|---|---|
| 4,725,670 A | 2/1988 | Grill et al. .................. 530/326 |
| 4,883,861 A | 11/1989 | Grill et al. .................. 530/326 |
| 5,474,796 A | 12/1995 | Brennan ..................... 427/2.13 |
| 5,759,785 A | 6/1998 | Tsai et al. .................... 435/7.1 |
| 5,767,075 A * | 6/1998 | Avruch et al. ................ 514/12 |

OTHER PUBLICATIONS

B. Sarkar et al, Genet. Response Met. Proc. Int. Symp. Met. Genet. 1st, Meeting Date 1994, 237–353.*
J. Hanas et al, Nucleic Acids Res., 24(5), 924–930 (1996).*
Kang et al., "Analysis of the Conformational Change of Recombinant Human Papilloma Virus Type 18 E7 Protein Induced by Metal Binding," *Virus Researc*, 49:147–154, 1997.
J. Berg, "Zinc Finger Domains: Hypotheses and Current Knowledge," *Annu. Rev. Biophys. Biophys. Chem.*, 19:405–21, 1990.
P. Eis, "Fluorescence Studies of Zinc Finger Peptides and Proteins," *Methods in Enzymology*, 278:330–343, 1997.
Godwin et al., "A Fluorescent Zinc Probe Based on Metal–Induced Peptide Folding," *J. Am. Chem. Soc.*, 118:6514–6515, 1996.
J. Berg, "On the Metal Ion Specificity of Zinc Finger Proteins," *J. Am. Chem. Soc.*, 111:3759–3761, 1989.

Irie et al., "Protein Kinase C Regulatory Domain Surrogate Peptides: Effects of Metal Ions on Folding, Phorbol Ester–Binding, and Selectivity," *Biorganic & Medicinal Chemistry Letters*, 7(8):965–970, 1997.
Giuliano et al., "Fluorescent–protein Biosensors: New Tools for Drug Discover," *Trends in Biotechnology*, 16(3):135–140, Mar. 1998.
Veenstra et al., "Zinc–Induced Conformational Changes in the DNA–Binding Domain of the Vitamin D Receptor Determined by Electrospray Ionization Mass Spectrometry," *Journal of the American Society for Mass Spectrometry*, 9(1):8–14, Jan. 1998.
Hanas et al., "Conformational States of Xenopus Transcription Factor IIIA", *Biochemistry*, vol. 28, No. 9, pp. 4083–4088, 1989.
Simons et al., "Arsenite and Cadmium (II) as Probes of Glucocorticoid Receptor Structure and Function", *The Journal of Biological Chemistry*, vol. 265, No. 4, pp. 1938–1945, Feb. 5, 1990.
Vallee et al., "Zinc Fingers, Zinc Clusters, and Zinc Twists in DNA–Binding Protein Domains", *Proc. Natl. Acad. Sci. USA*, vol. 88, pp. 999–1003, Feb. 1991.
Cho et al., "Crystal Structure of a p53 Tumor Suppressor–DNA Complex:Understanding Tumorigenic Mutants", *Science*, vol. 265, pp. 346–355, Jul. 15, 1994.
Schena et al., "Quantitative Monitoring of Gene Expression Patterns with a Complementary DNA Microarray", *Science*, vol. 270, pp. 467–470, Oct. 20, 1995.
Schena et al., "Parallel Human Genome Analysis: Microarray–Based Expression Monitoring of 1000 Genes", *Proc. Natl. Acad. Sci. USA*, vol. 93, pp. 10614–10619, Oct. 1996.
Shoemaker et al., "Quantitative Phenotypic Analysis of Yeast Deletion Mutants Using A Highly Parallel Molecular Bar–Coding Strategy", *Nature Genetics*, vol. 14, pp. 450–456, Dec. 14, 1996.
Hacia et al., "Detection of Heterozygous Mutations in BRCA1 using High Density Oligonucleotide Arrays and Two–Colour Fluorescence Analysis", *Nature Genetics*, vol. 14, pp. 441–447, Dec. 14, 1996.
DeRisi et al. "Use of cDNA Microarray to Analyse Gene Expression Patterns in Human Cancer", *Nature Genetics*, vol. 14, pp. 457–460, Dec. 14, 1996.
John Travis, "Chips Ahoy. MicroChips Covered with DNA Emerge as Powerful Research Tools", 9 *Science News*, vol. 151, pp. 144–145, Mar. 8, 1997.

* cited by examiner

*Primary Examiner*—Mary E. Ceperley
(74) *Attorney, Agent, or Firm*—Dunlap, Codding & Rogers, P.C.

(57) ABSTRACT

The present invention is a method and kit for analyzing a sample, preferably a liquid environmental sample, which may comprise a toxic xenobiotic element or compound, i.e., an environmental pollutant. The method and kit preferably utilize a portion of a molecule comprising a peptide zinc binding domain, known as a zinc finger.

8 Claims, 13 Drawing Sheets

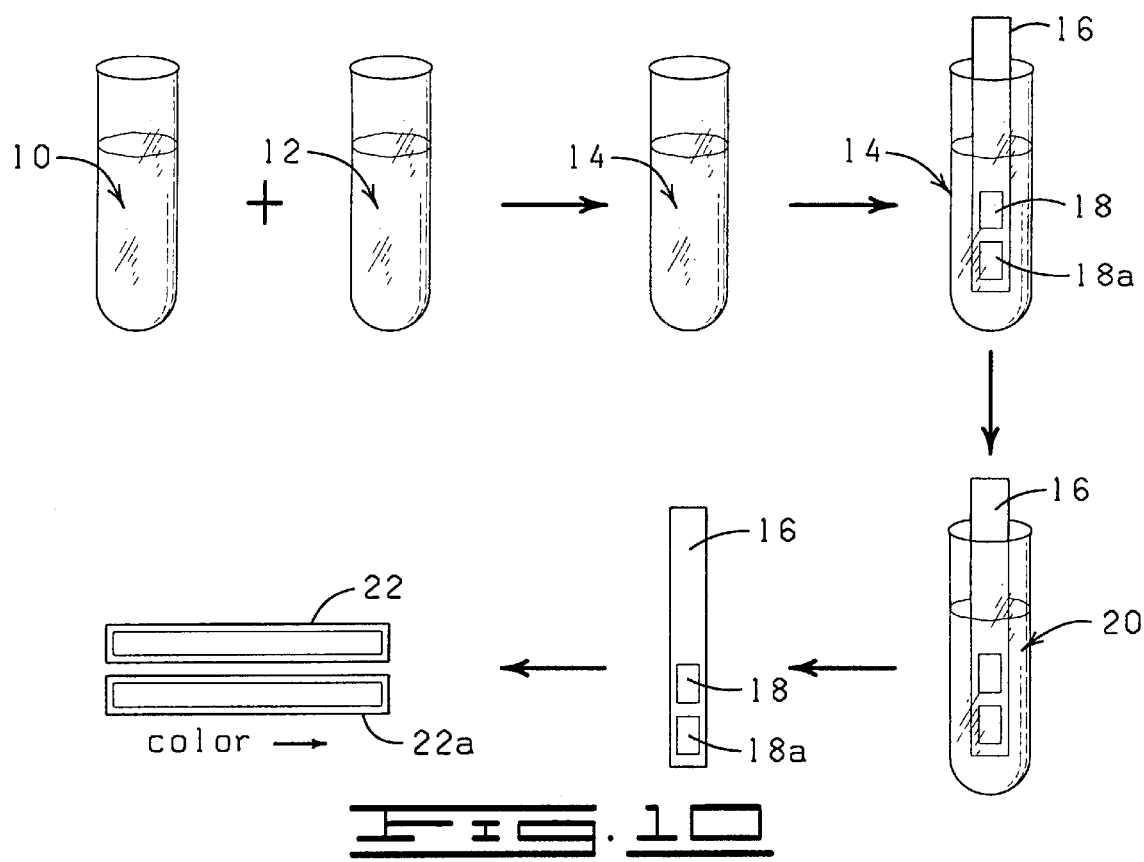
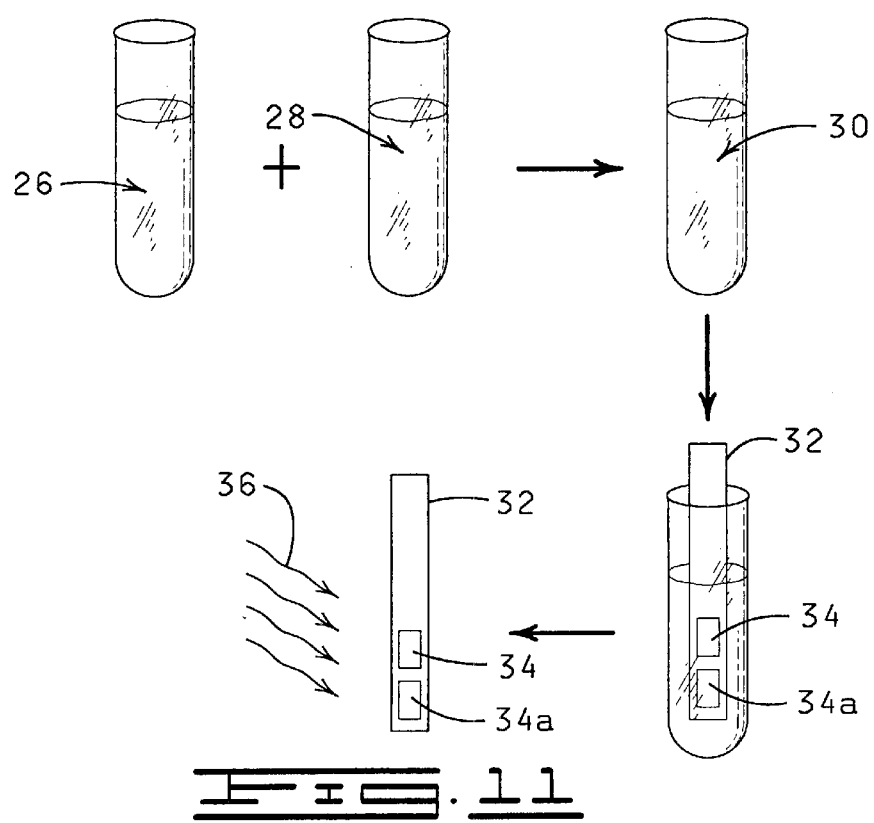

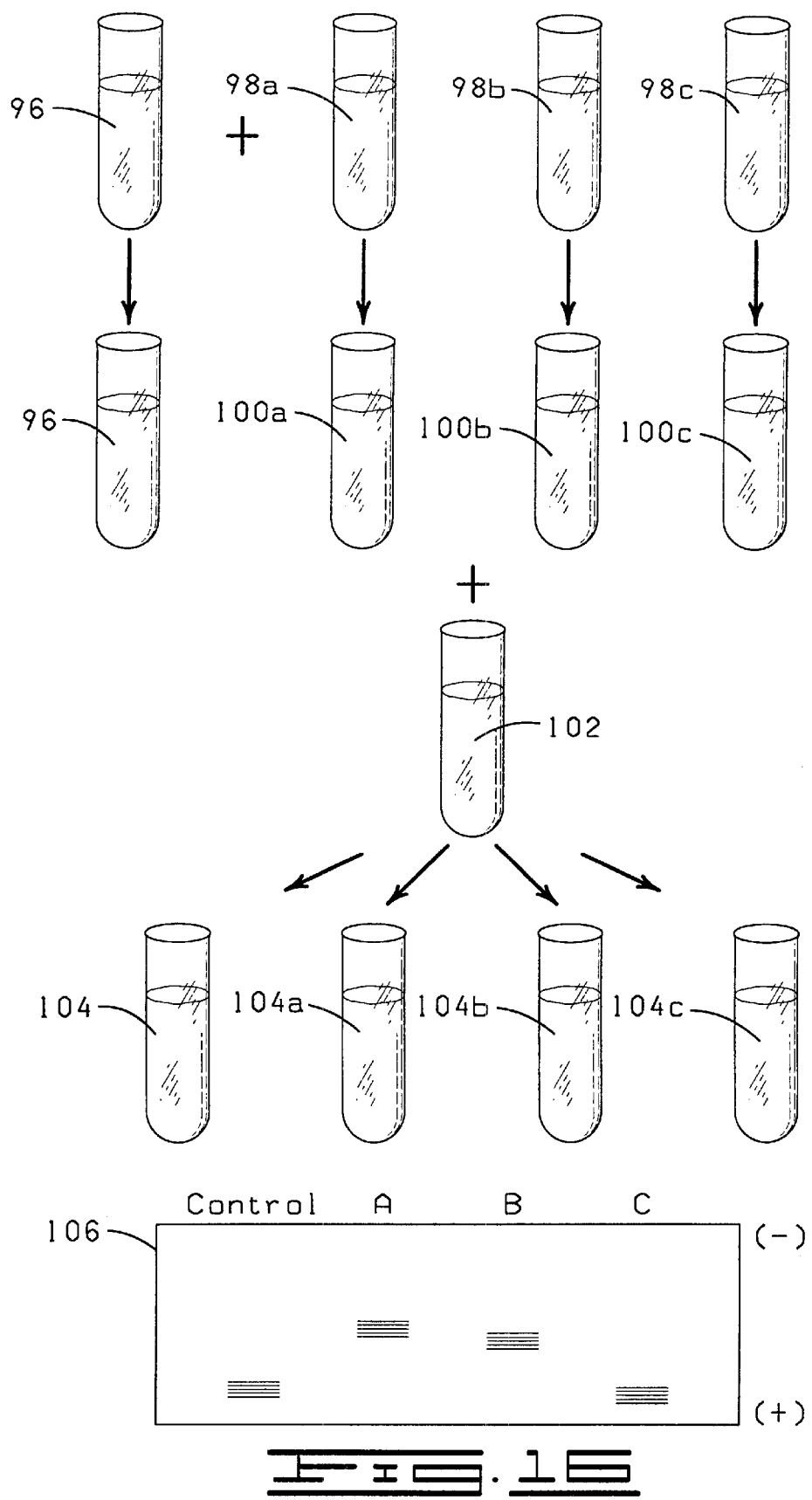

TEST FOR DETECTING SUBSTANCES WHICH ALTER THE CONFORMATIONAL STRUCTURE OF ZINC FINGERS

CROSS-REFERENCE TO RELATED APPLICATIONS

This application is a continuation of U.S. Ser. No. 09/034,705, filed Mar. 4, 1998, entitled "TEST FOR DETECTING SUBSTANCES WHICH ALTER THE CONFORMATIONAL STRUCTURE OF ZINC FINGERS", now U.S. Pat. No. 6,235,538, issued May 22, 2001; which claims priority under 35 U.S.C. §119(e) of U.S. Provisional Application Ser. No. 60/039,873, filed Mar. 5, 1997.

STATEMENT REGARDING FEDERALLY SPONSORED RESEARCH OR DEVELOPMENT

Not Applicable

BACKGROUND

The present invention is related to methods of testing samples for environmental contaminants, in particular, for xenobiotic contaminants, using zinc fingers.

The chemical toxic load in the environment has steadily increased over the past 50 years due to increased industrialization, manufacturing, and technology advancement. Most of the chemical agents, including xenobiotics or environmental chemicals of a non-physiological origin, pose major health risks. Therefore, the detection and monitoring of such potentially dangerous chemical toxins is becoming increasingly important and necessary.

It is well known that environmental chemicals of a non-physiological origin (xenobiotics), as well as chemicals which mimic physiological compounds can have deleterious effects on human biology. As used herein, the term "xenobiotic" refers to those elements or compounds which are potentially toxic to biological systems, including elements and compounds having no physiological or biological origin or utility and those elements and compounds which may have biological origin or utility but which at some concentration have biologically inhibitory effects. Because of rapid industrialization and the accompanying waste generation and land reclamation, the detection and monitoring of harmful pollutants is becoming increasingly important and necessary.

The xenobiotic metal cadmium, for example, is believed to be an environmental factor and/or contributor to a variety of human disorders, such as carcinogenesis, teratogenesis, organ failure (kidney), neurological disorders, and immunosuppression. With respect to DNA transcription events, cadmium has been shown to bind chromatin and induce jun and myc oncogene expression. The striking effect of cadmium on TFIIIA-type zinc fingers, as discussed herein below, also points to a role for cadmium in the alteration of gene expression in vertebrates. Also, aluminum is one of the most abundant elements in the earth's crust and is a known neurotoxin. It has also been implicated in the etiology of Alzheimer's disease (AD) and other neuronal disorders.

Based upon these two xenobiotics alone, the sites and resources that require regular biomonitoring are almost limitless.

Various approaches for xenobiotic analyses exist, including classical chemical and living animal studies. Chemical analyses usually involve atomic absorption spectroscopy for metals, and gas chromatography-mass spectroscopy for analyzing organics and inorganics. Rodent systems are the most popular living animals for such analysis. Unfortunately, these chemical and biological studies are time-consuming and quite expensive, thereby negating large scale use which is necessary for extensive detection and biomonitoring. Classical methods of detection may provide information about the concentrations environmental pollutants, but they do not provide direct information on the biological targets or harmful consequences of such agents on vertebrates. Biomonitors and biomarkers can provide such qualitative information, however, most involve fairly complicated, expensive, and time-consuming procedures which typically use living animals or cells.

Because of these unwieldy concerns for pollution analyses with classical chemical and biological systems, other biomonitoring approaches and systems have been developed. One such biomarker approach analyzes DNA adduct formation which results from human exposure to polycyclic aromatic hydrocarbons (Mumford et al., 1993, *Environ. Health Pers.*, 99:83). The methodology for adduct analysis utilizes both fluorescence and immunological assays in a complicated and time consuming process. Two other biomonitor approaches, Microtox™ and Artoxkit™ pollution analysis systems have been developed. The Microtox™ test utilizes the marine bacterium Photobacterium phosphoreum which radiates bioluminescence under appropriate conditions (Microbics Corporation, 1982, Manual 555880-R1, Carlsbad, Calif.). The bacterium is exposed to various concentrations of a suspected pollutant and any reduction in bioluminescence is measured with a luminometer. The Artoxkit™ test utilizes larvae of the brine shrimp Artemia salina and assays the effects of pollutants on larvae motion (Persoone and Wells, 1987, *Artemia Research and Its Applications*, Vol.1-Morphology, Genetics, Strain Characterization, Toxicology, Universa Press, Wetteren, Belgium).

Recently, a study demonstrated that neither of the Microtox™ or Artoxkit™ test kits were as sensitive in detecting herbicides as with a traditional algae assay system (Gaggi et al., 1995, *Environ. Toxicol. Chem.*, 14:1065). The algae test system, however, requires sterile conditions and extensive cell growth studies. These cellular pollution analysis systems inherently include the additional variable of the relevancy of the physiological process assayed (e.g. bioluminescence) to human biology. Cellular assays, although obviously easier to work with than rodent systems, are relatively cumbersome compared with an in vitro system which is able to inexpensively assay a large number of samples in a relatively short period of time.

In 1983, it was discovered that cysteine-rich eukaryotic regulatory proteins contain zinc-binding domains and require the zinc ion for function (Hanas et al., *J.Biol.Chem.*, 258:14120). These zinc binding domains were subsequently termed "zinc fingers." A eukaryotic regulatory protein discovered to contain zinc was transcription factor IIIA (TFIIIA), a protein which regulates ribosome synthesis. Each of nine zinc fingers in this protein contains two cysteine (Cys) and two histidine (His) amino acids which bind to a zinc ion.

The $Zn^{2+}$ ions hold the structure together, since their removal results in unfolding of TFIIIA and concomitant loss of specific DNA binding ability. Crystallographic analysis of TFIIIA-type $Cys_2His_2$ zinc finger domains bound to DNA revealed compact finger domains wrapped around the major groove. The centrally located $Zn^{2+}$ ion in each finger was coordinated by the two Cys residues in an antiparallel β-sheet and by the two His residues located on the same face of an α-helix. Residues in the α-helix interact specifically via hydrogen bonds with base pairs in the DNA, whereas other amino acids throughout the domain make ionic contacts on DNA phosphates. Mutagenesis of TFIIIA revealed the necessity for all four metal coordinating residues, as well as the integrity of interfinger linker regions, for specific DNA binding. Proteins containing TFIIIA-type zinc finger domains ($Cys_2His_2$) are now known to number in the thousands in vertebrates and constitute the largest known superfamily of proteins in all organisms. TFIIIA-type zinc finger proteins regulate a multitude of processes, including embryogenesis and oncogenesis.

The steroid hormone receptor superfamily comprises another large group of cysteine-rich zinc finger transcription factors which translocate into the nucleus upon hormone binding. These proteins activate expression from enhancer regions of a number of hormone responsive genes. Unlike the TFIIIA superfamily, the DNA binding domains of hormone receptors always contain just two $Cys_2Cys_2$ zinc fingers. The first finger and linker region comprise an α-helix and make specific DNA contacts in the DNA major groove, whereas the second finger is involved in protein-protein interactions forming the active receptor dimer. Because of the cysteine-rich nature of the DNA binding domains of steroid hormone receptors, studies have examined the effects of metals other than zinc on the structure and function of hormone receptors. Such studies have added significance since a number of metal ions, including xenobiotic ions, are believed to have etiological roles in carcinogenesis and other disease processes. For example, with respect to the estrogen receptor (ER), one study indicated that 1 mM $Cd^{2+}$ could inhibit DNA binding by activated (hormone-bound) receptors and 0.1 mM $Cd^{2+}$ could inhibit initial binding of hormone to receptor (S. S Simons, P. K Chakraborti and A. H. Cavanaugh, *J. Biol. Chem.*, 1990, 265, pp. 1938–1945). Another study demonstrated that $Cd^{2+}$ could replace zinc in the ER and suffice for DNA binding, although some functional variation was observed (P. F. Predki and B. Sakar, *J. Biol. Chem.*, 1992, 267, pp. 5842–5846).

Amino acids between the second metal-coordinating Cys residue and the second metal-coordinating His residue bind DNA in a sequence-dependent manner. The nine zinc fingers of TFIIIA bind the internal control region (ICR) of the 5S RNA gene (nucleotides +43 to +96). The fingers appear to bind in groups of three with the N-terminal group binding to the 3' C-box of the ICR, the middle group binding in M-box, and the C-terminal three binding the A-box. Binding of the middle and C-terminal finger groups is dependent upon initial binding of the N-terminal group. Mutations in zinc-binding residues in the N-terminal fingers abolish TFIIIA binding whereas similar mutations in the more C-terminal fingers still allow binding by the N-terminal finger group. Zinc ions can be removed from TFIIIA, leading to unfolding of the protein and loss of specific DNA binding ability. Proteins in the TFIIIA superfamily differ in their number of zinc fingers and also in their amino acid sequences, thereby leading to differing DNA binding specificities. Prominent members of the TFIIIA superfamily (e.g. EGR1 family) control cell growth, differentiation, and embryogenesis. Alterations in several of these $Cys_2$ $His_2$ zinc finger proteins cause tumorigenesis and teratogenesis. For example, mutations in one such protein, Wilms' tumor suppressor, cause a pediatric kidney tumor. The functions of the majority of the TFIIIA superfamily, however, are unknown.

Many other cysteine-rich factors known in the art contain zinc fingers although of slightly different structure than that found in TFIIIA. All the different kinds of cysteine-rich zinc finger proteins number in the thousands in vertebrates and are known to constitute the majority of the regulators of gene expression and signaling. Biochemically, cysteine-rich zinc finger domains perform specific interactions with DNA, RNA, and proteins. Because zinc ions are not tightly bound to the cysteine residues in such proteins, and because of the high reactivity of cysteine in the reduced form, zinc finger proteins are likely to be susceptible to conditions which interfere with zinc binding leading to inhibition and/or alteration of the zinc finger functional ability, thereby resulting in deleterious effects on cell function and organ physiology. In addition, the agents which harm cysteine-rich zinc finger proteins may also affect other cellular proteins, including those containing critical cysteine residues and other nucleophilic amino acid side chains like imidazole, hydroxyl, amides, carboxyl, and amines. Because these effects pose major health risks, it is important and necessary to develop rapid assay methods to detect and monitor xenobiotic agents in the environment which have the potential to harm zinc finger proteins.

BRIEF SUMMARY OF THE INVENTION

The present invention describes rapid and inexpensive biomonitor test for aiding in the detection and monitoring of potentially toxic chemicals such as xenobiotics in environmental samples which have potential harmful effects on humans. Other biological samples may also be tested. This invention relies on the use of the extreme conformational sensitivity of zinc finger proteins or peptides to the presence of xenobiotics.

BRIEF DESCRIPTION OF THE DRAWINGS

FIG. 10 is a schematic of an enzyme-linked substrate assay for use in the present invention.

FIG. 11 is a schematic of a fluorescence assay for use in the present invention.

FIG. 16 is a schematic of a gel shift assay for use in the present invention.

DETAILED DESCRIPTION OF THE INVENTION

Figure 1:
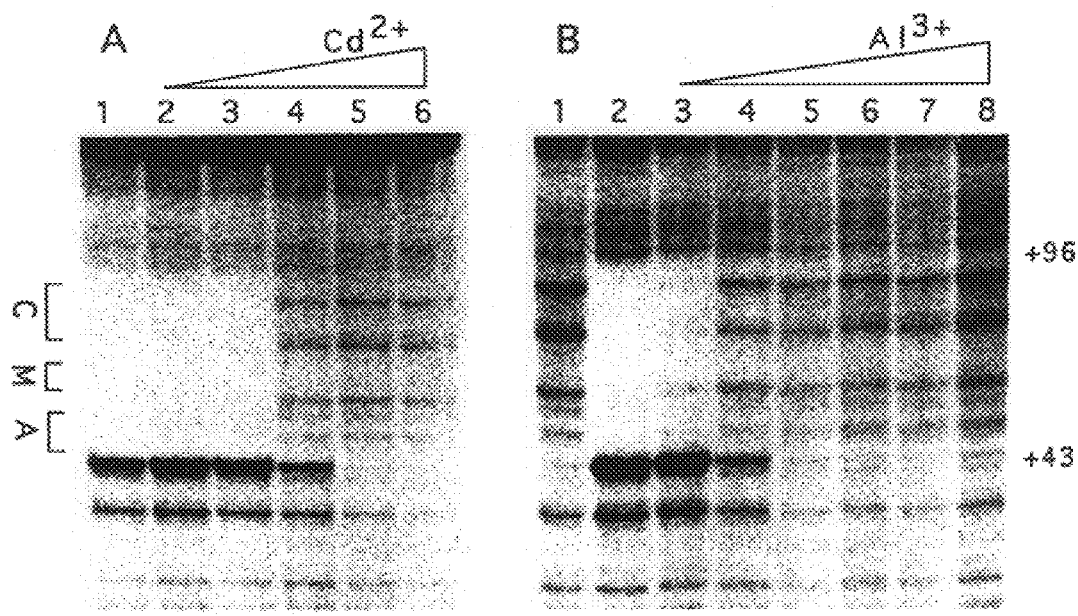
FIG. 1 is an autoradiogram of a DNase I protection assay on acrylamide-urea gel showing the effects of cadmium and aluminum ions on the binding of TFIIIA zinc finger to the Xenopus 5S ribosomal gene.

The present invention comprises a method and kit for analyzing a sample, preferably a liquid, which may comprise a toxic xenobiotic element or compound. The method and kit utilize a portion of a molecule comprising a zinc binding domain, known as a zinc finger. The zinc finger is any cysteine-rich and/or histidine rich potential zinc binding portion of a protein or peptide which has affinity binding for another protein or peptide or for a nucleic acid fragment.

Where used herein, the term "zinc finger" refers to (1) any cysteine-rich and/or histidine rich three-dimensional domain of a protein or peptide involved in nucleic acid or protein template binding, wherein the domain comprises amino acid residues which bind to zinc, or which are involved in binding to the template, and (2) to any cysteine-rich portion of a protein or peptide which does not bind to zinc, but the conformational structure of which is altered by a xenobiotic as defined herein. More specifically, a zinc finger comprises a peptide or polypeptide comprising at least three metal binding amino acid residues, further comprising two or more cysteine residues and from zero or more histidine residues which can be folded around a zinc ion for binding thereto. For a TFIIIA protein for example, the functional binding unit comprises a unit of from one to three to nine TFIIIA zinc fingers, each of which comprise about 30 amino acids, which binds to a DNA sequence. Where used herein the term zinc finger may refer to only a single zinc finger or to several zinc fingers functioning together as a single binding unit. However, in those embodiments of the present invention not relying on the binding of a zinc finger to a nucleic acid or protein template, it is only necessary that the conformation of the zinc finger be altered in a detectable manner. This may be feasible with a single zinc finger (even for a TFIIIA zinc finger), for example when the zinc finger is bound to a chemical group such as I-AEDANS(N[[iodoacetyl)amino]ethyl]-5-naphthylamine-1-sulfonic acid).

Other categories of zinc finger proteins include members of the steroid hormone receptor superfamily. These receptors are transcription factors that regulate the expression of hormone-responsive genes. All members of this superfamily contain two zinc fingers of the $Cys_2Cys_2$ type. The first finger is involved in specific DNA binding and the second finger is involved in protein-protein interactions. The tumor suppressor p53 is also classified as a zinc finger protein. Protein p53 regulates cellular response to DNA damage by halting the cell cycle to allow repair of DNA damage before this damage is replicated and passed on to progeny cells. This protein has a highly conserved cysteine-rich region (which also contains a histidine) that X-ray crystallography demonstrates folds around a zinc ion, forming a core DNA binding domain. The core DNA/Zinc binding domain of p53 extends from residues 102–292 thereof, comprising the central conserved portion of the protein. The cys 277 residue, although apparently not functional in binding to the zinc ion, may bind to a xenobiotic, thereby altering the conformation and DNA binding ability of the zinc finger without affecting binding of the zinc ion. Point mutations leading to tumorigenesis are prevalent in this DNA binding domain. Importantly, mutations in the four p53 zinc-binding residues (cysteines 176,238,242 and histidine 179) all result in tumorigenesis. Overall, p53 mutations are the most prevalent genetic changes in human carcinomas. Structural alterations in p53 would allow the cell cycle to continue in the presence of DNA damage and thus increase the likelihood of transmitting oncogenic changes to daughter cells. Mutated or structurally altered p53 would also not be able to induce apoptosis.

Wild-type p53 arrests the cell cycle in the $G_1$ phase of mitosis by inducing the expression of the cyclin-dependent kinase inhibitor Cipl/Wafl. The kinase inhibitor binds to and inhibits a cyclin-dependent kinase (cdk2) whose phosphorylation activity is necessary for progression from $G_1$ into the S phase of the cell cycle. Cipl, also referred to as p21, binds cdk2 with its highly conserved N-terminal domain, amino acids 13 to 71 (Conserved cysteine-rich cdk2 binding domain in Cipl/Wafl/p21). Significantly, this region in human p21 also has a highly conserved, potential zinc finger in which four cysteine residues (but 3 Cys and 1 His in rodents) are positioned to coordinate a zinc ion. Unlike the zinc fingers in p53 and TFIIIA, the p21 cysteine-rich domain is apparently not involved in protein-nucleic acid interactions but rather in protein-protein interactions. Importantly, this major pathway regulating cell growth contains two cysteine-rich regulatory proteins that act in concert.

Because zinc ions are not covalently bound to cysteine residues in zinc fingers and because of the high nucleophilic reactivity of the cysteine SH group, zinc finger peptides and proteins are susceptible to identifiable chemical alterations induced by xenobiotic agents. Xenobiotic agents which affect or cause substitutions in zinc fingers also could affect other cellular proteins containing critical cysteine residues as well as other nucleophilic amino acid side chains like imidazole, hydroxyl, amides, carboxyl, and amines. Cysteine residues in particular may be the Achilles' heel of cellular physiology. In particular, the cysteine-rich nature of the p53-p21 pathway for regulating cell proliferation may be susceptible to such structural changes with deleterious consequences including the initiation of hyperproliferative diseases.

Although the assay described herein was designed to assay environmental pollutants in water and soil samples, it has other applications for chemical and health-related industries as well as academia. Animal studies are presently used to routinely assay toxic effects of known pesticides, herbicides, and other chemical products (at their site of manufacture) which are known to come into human contact. The present test could augment and in some cases replace such procedures. Testing of drugs for human use also relies heavily on animal toxicity studies and the present test could augment these as well. Toxicology research and education applications would also potentially benefit from the present test. Because the present test is extremely sensitive to cadmium, the development of a test kit could allow heavy smokers to self-monitor cadmium in bodily fluids. Other home uses of such a kit would include the pollution monitoring of water and soil samples.

As explained in further detail below, a number of in vivo environmental biomonitor tests are commercially available. Therefore, a sizable market already exists for such testing procedures. TFIIIA, for example, is an extremely stable protein (DNA binding activity survives boiling for several minutes) which is useful as a practical matter for any kit application. Such a kit would have widespread applicability in government, industry, university, and residential settings. As individuals become more and more concerned about their exposure to environmental pollutants, the desire to identify where that exposure is coming from will proportionally increase.

The kit claimed herein comprises a set of components for use in any of the methods contemplated herein which rely on use of a zinc finger for determining presence, absence, or relative concentration of a xenobiotic in a test sample such as a sample derived from an environmental source (e.g., water) or from a biological fluid such as blood, urine, or any biological secretion. The xenobiotic is any element, compound or chemical of non-biological origin which can affect the conformational structure or binding capacity of the zinc finger; examples are cadmium ions ($Cd^{2+}$), aluminum ions ($Al^{3+}$), lead ions ($Pb^{2+}$), and selenium ions ($Se^{4+}$). Other examples of xenobiotics are herbicides, pesticides, and fungicides, for example, and may include organophosphates, methyl parathion, malathion, carbamates including carbanyl and aldicarb, and pyrethroids such as cypermethrin.

In a preferred embodiment, the invention comprises a method of testing a sample for the presence of a xenobiotic element or compound, including the steps of providing a test sample, providing an amount of a zinc finger having a characteristic native conformational structure, treating the zinc finger with the test sample to form a treated zinc finger, and concluding that a xenobiotic element or compound is present in the test sample when there is a difference between the conformational structure of the treated zinc finger and the native conformational structure of the zinc finger. The zinc finger may be derived from a protein selected from the TFIIIA superfamily, human tumor suppressor protein p53, GATA1, cdk inhibitor protein p21, BRCA 1, and the steroid hormone receptor family or other cys/his-rich regulator proteins. One or more different types of zinc fingers which are treated with the test sample may be provided.

The method may further comprise providing an amount of a template for which the zinc finger has binding affinity, exposing the treated zinc finger to the template for determining the binding affinity of the treated zinc finger for the template, and concluding that the conformational structure of the treated zinc finger is different from the native conformational structure of the zinc finger when the binding affinity of the treated zinc finger for the template is less than the binding affinity of the zinc finger for the template. Also in this version, at least two different types of zinc fingers which are treated with the test sample may be provided. A template for each different type of zinc finger may be provided. The template may be selected from the group consisting of DNA, RNA, protein or a peptide. In one embodiment, the zinc finger has an enzyme linked thereto. In such a case, a substrate reactive with the enzyme linked to the zinc finger for treating the template to which the treated zinc finger has been exposed may be provided. In another version, the zinc finger may have a fluorescent label linked thereto, in which case the method may further comprise the step of irradiating the template to which the treated zinc finger has been exposed with an excitation wavelength of light for causing emission of an emission wavelength of light from the zinc finger. Where provided the template may be disposed on a support surface, which preferably comprises cellulose, glass, plastic, or metal, or combinations thereof.

The method of the present invention may comprise the additional step of exposing the template to which the treated zinc finger has been exposed to enzyme-linked antibodies, wherein the template to which the treated zinc finger has been exposed will in turn be exposed to a substrate reactive with the enzyme of the enzyme-linked antibody. The method, in another version, may comprise the additional steps of exposing the template to which the zinc finger has been exposed to a cleavage enzyme for producing cleavage fragments of the template and assaying the cleavage fragments which result from the action of the cleavage enzyme.

Alternatively, the zinc finger may be further defined as comprising a zinc finger complex which when illuminated with an excitation wavelength causes a fluorescence emission and wherein the difference in the conformational structure of the treated zinc finger and the native conformational structure of the zinc finger is detectable by a difference in the intensity of the fluorescence emission from the treated zinc finger and the fluorescence emission from the zinc finger when illuminated by the excitation wavelength. In this case, the zinc finger complex may comprise the chemical moiety I-AEDANS.

The present invention further comprises a kit for testing a sample for the presence of a xenobiotic element or compound. The kit may comprise an amount of a zinc finger which has a binding affinity for a template, an amount of the template, means for combining the zinc finger and a test sample to form a reaction mixture, and means for combining the reaction mixture with the template. The zinc finger of the kit may have a fluorescent label attached thereto. The kit may further comprise a quantity of an enzyme-linked antibody for combining with the zinc finger. The kit may further comprise a quantity of a substrate for reacting with the enzyme linked to the antibody.

Alternatively, the zinc finger of the kit may have an enzyme linked thereto, and may further comprise a quantity of substrate for reacting with the enzyme linked to the zinc finger. Also, the kit may comprise a quantity of an enzyme for fragmenting the template for further analysis. The template may comprise DNA, RNA, peptides and proteins.

Alternatively, the kit may comprise an amount of a zinc finger complex having a characteristic conformational structure, and which when illuminated with an excitation wavelength has a characteristic fluorescence emission intensity, and having a different fluorescence emission intensity when the characteristic conformational structure is altered by a xenobiotic, and means for combining the zinc finger complex with a test sample to form a treated zinc finger complex for measuring a fluorescence emission of the treated zinc finger complex.

In one embodiment a plurality of different characteristic templates, including peptides, proteins or nucleic acid fragments may be adhered to a support surface such as treated glass or metal to provide a "microarray" or "gene chip" of templates for reacting with a plurality of corresponding zinc fingers. Dozens, hundreds, or thousands of templates (identical or different) may be applied to the support surface. Methods of forming such microarrays are known to those of ordinary skill in the art, for example, in M. Schena, D. Shalon, R. Davis and P. Brown, "Quantitative Monitoring of Gene Expression Patterns with a Complementary DNA Microarray", *SCIENCE,* Vol. 270, pp. 467–470, (Oct. 20, 1995), which is incorporated by reference herein in its entirety. These "microarrays" may be used in any of the embodiments described herein to which such a system can be adapted, as can be understood by one of ordinary skill in the art.

Particular zinc fingers may be selectively inhibited only by specific xenobiotics or by combinations of xenobiotics. The TFIIIA zinc finger, for example, is known to be affected by Cd, Pb, Al and Se, but not by Hg, Cs or Mn. Another zinc finger may be inhibited only by Pb and Se. A third zinc finger may be inhibited only by Al and Pb. A test sample which Inhibited all three zinc fingers could be concluded as comprising Pb. A test sample which inhibited the first and second zinc fingers could be concluded as comprising at least one of Cd and Se. It can be appreciated that it would be well within the ability of a person of ordinary skill in the art to identify an array of such selectively-inhibited zinc fingers and to combine them to construct a single qualitative test for determining the presence of particular xenobiotics.

Enzyme-linked assays are well known to those of ordinary skill in the art, as exemplified by the disclosure of E. Engvall and P. Perlman in "Enzyme-linked immunosorbent assay (ELISA): quantitative assay of immunoglobulin G., *Immunochem.*, 8, 871–879 (1971), which is incorporated by reference herein in its entirety. Such assays and their use in the present invention are described in more detail below.

In an alternative embodiment the analysis of the zinc finger treated with the test sample may be performed using mass spectroscopy. For example, the treated zinc finger may be placed on a support surface (e.g., metal) and analyzed using laser mass spectroscopy. Alternatively, the zinc finger may be preapplied to the support surface (e.a. in a microarray) and then treated with the test sample. The zinc fingers thus tested can be analyzed for changes in mass and thereby identified as to the xenobiotic binding thereto.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Inhibition of Zinc Finger Binding by Cadmium and Aluminum

As shown herein, the $Cys_2$ $His_2$ zinc finger structure of TFIIIA is highly sensitive to inhibition by certain xenobiotic metal ions such as cadmium and aluminum. Inhibition of TFIIIA binding to the 5S ribosomal RNA gene was assayed by the DNase I protection method. The results are shown in FIG. 1. In this assay, TFIIIA isolated from frogs, or as a recombinant protein, was incubated for a short period of time with a radioactively labeled double-stranded DNA fragment containing the 5S ribosomal RNA gene sequence (120 base-pairs in length). In TFIIIA's role in regulating ribosome synthesis, the protein birds specifically and tightly to this 5S gene sequence. When this occurs, the bound protein protects a large region of the 5S RNA gene from DNase I digestion. DNase I normally degrades the 5S gene and in the process generates a series of differently sized DNA fragments which can be resolved by electrophoresis. TFIIIA binding protects a DNA region comprising approximately 53 base pairs from DNase I degradation.

Cadmium and aluminum inhibition of TFIIIA binding was ascertained by observing the loss of this protected region from 5S gene nucleotides (+43 to +96). FIG. 1 shows the concentration dependence of $Cd^{2+}$ and $Al^{3+}$ ion inhibition of TFIIIA-5S RNA gene interactions.

In panel A of FIG. 1, the presence of a complete vertical banding pattern is indicative of a lack of TFIIIA binding to the 5S gene (lanes 4–6) whereas the presence of the large gap in this banding pattern indicates where TFIIIA is specifically binding (lanes 1–3). TFIIIA binding is inhibited by 0.1 μM cadmium ions (lane 4, panel A) and 3 μM aluminum ions (lane 4, panel B); this inhibition is irreversible and not overcome by added zinc ions. These metal ion concentrations are 100–1000 times lower than previously observed to be inhibitory in other in vitro enzyme systems. Most significantly, the cadmium concentration is approaching that found in the blood of heavy smokers. This result indicates TFIIIA zinc finger structure is uniquely sensitive to xenobiotic metals and other environmental agents which affect zinc binding. Of note, the metal sensitivity of this assay can be increased by longer TFIIIA exposure times (more than 15 min, as was the case with the metal ions) and/or increasing the temperature of the exposure reaction.

Inhibition of TFIIIA binding (i.e., loss of DNase I protection between nucleotides +43 and +96) is almost complete at 0.1 μM $Cd^{2+}$ (lane 4), although some binding is still occurring, as evidenced by the DNase I hypersensitive site at +43. Therefore, <10 molecules of $Cd^{2+}$ per TFIIIA molecule are inhibitory. Complete loss of this TFIIIA-dependent DNase I hypersensitivity, as well as DNase I protection up to nucleotide +96 on the coding strand, is observed in the 0.25 μM sample (lane 5). FIG. 2B exhibits the $Al^{3+}$ dose-response inhibition of TFIIIA binding to the 5S RNA gene (lanes 1 and 2 are minus and plus TFIIIA binding controls). Slight inhibition of TFIIIA binding by $Al^{3+}$ ions is observed at 1 μM (lane 3) and complete inhibition is observed in the 5–7 μM range (lanes 5 and 6). This inhibitory concentration of $Al^{3+}$ is about 50-fold greater than that for $Cd^{2+}$.

EXAMPLE 2

Testing of Environmental Water Samples

Figure 2:
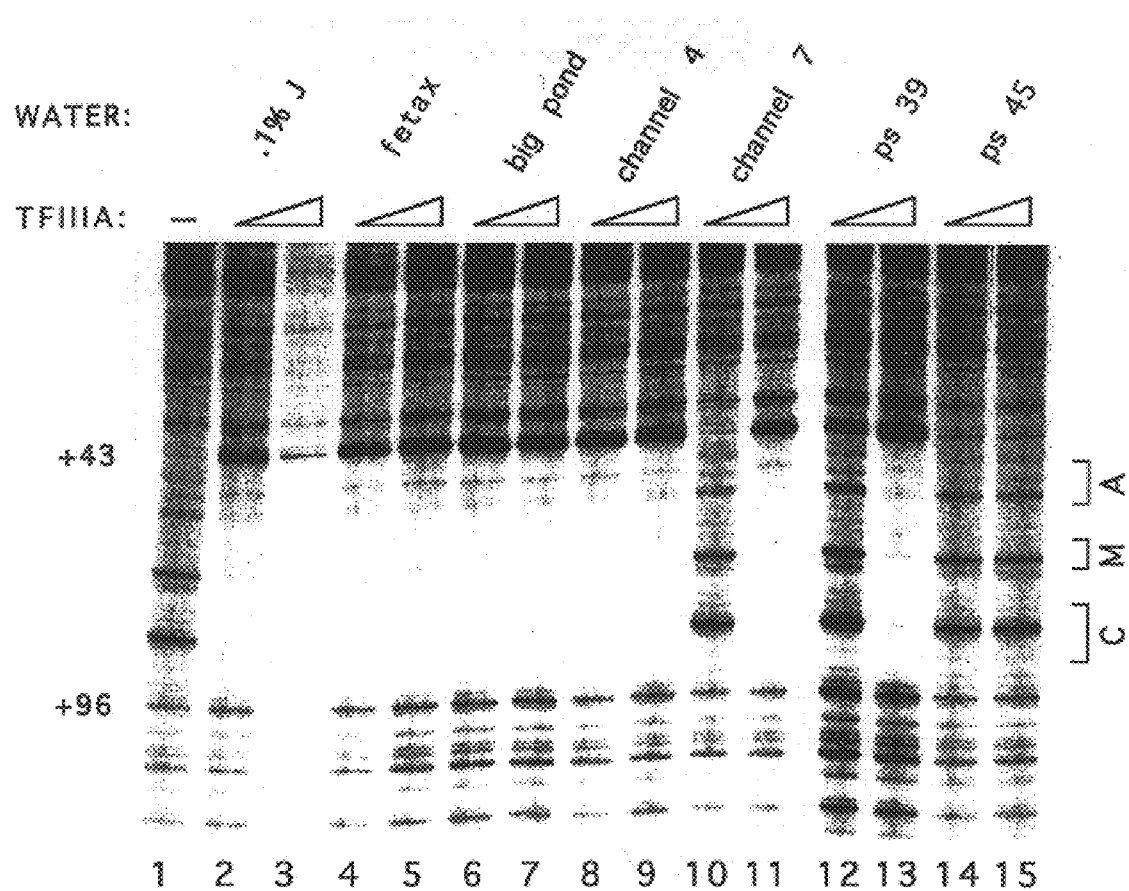
FIG. 2 is an autoradiogram of a DNase I protection assay on acrylamide-urea gel showing the effects of environmental water samples on the binding of TFIIIA zinc finger to the Xenopus 5S ribosomal gene.

This extreme sensitivity of TFIIIA to inhibition by these xenobiotics indicates this assay (termed the ZifTox test, a constriction of "zinc finger toxicity") can be useful for biomonitoring of environmental xenobiotics. To test the usefulness of the ZifTox TFIIIA DNA binding assay in detecting harmful xenobiotic agents, an experiment utilizing water samples from an environmental site known to comprise toxic materials was performed. Water samples were obtained from ponds and channels from this sanitary landfill in Norman, Okla. This landfill has been designated a toxic waste site by the Environmental Protection Agency. FIG. 2 is an autoradiogram exhibiting the TFIIIA-dependent DNase I protection results from the analysis of a number of such water samples.

TFIIIA used in the reactions electrophoresed in lanes 2–15 was preincubated in the differing water samples listed above the lanes. 20 and 40 nM concentrations of TFIIIA were used for each water sample. The reaction electrophoresed in lane 1 contained only 32p end-labeled DNA. 0.1% J is the normal buffer used in the DNase I assay; fetax is the water used in the frog embryo toxicity assay; ps 39 and 45 are pump well sites at the landfill. Only water from channel 7 and pump sites 39 and 45 inhibited TFIIIA zinc fingers and these were also the only water samples listed that were lethal for frog embryo development in the fetax water.

Prior to addition to the 5S gene-DNase I protection reaction in the ZifTox test, TFIIIA was incubated for 15 minutes at room temperature in ¾ volume of the respective Norman landfill water samples (big pond, channels 4 or 7, small ponds 39 or 45), regular buffer (0.1%J), or fetax water. FETAX is the name of a frog embryogenesis-tetraogenesis assay developed by Dr. John Bantle from Oklahoma State University. Fetax water is the synthetic medium which the frog eggs hatch in and undergo development. Dr. Bantle has performed the FETAX assay using water samples collected from these locations as well as other locations from the Norman landfill. In this assay, embryogenesis and development of *Xenopus laevis* frogs in the various water samples is examined and scored for malformation or mortality. Of note, there exists a significant amount of embryo malformation (7.6%) in the control fetax water.

In the presence of the regular buffer or fetax water, TFIIIA binds normally to the 5S gene as evidenced by the DNase I protection from nucleotides +43 to +96 (lanes 2,3 and 4,5 respectively). The triangles above the pairs of lanes indicate that increased amounts of TFIIIA (2×) were added to the second lane. Also not affecting TFIIIA DNA binding under these assay conditions were water samples from the big pond and channel 4 of the Norman landfill (lanes 6,7 and 8,9). Of note, these two water samples had FETAX malformation rates of 12.5% and 19.4% respectively compared to the fetax water control rate of 7.6%. It is not known why such high control rates of malformation exist in the FETAX assay system.

These results with the ZifTox test indicate that untreated ground water is not generally inhibitory to TFIIIA function. Most significantly however, the pump site 45 water had a completely inhibitory effect on TFIIIA function (lanes 14,15). Importantly, this water sample caused 100% embryo mortality in the FETAX embryogenesis assay (all FETAX assay results were personal communications to the P.I. from John Bantle). This important result indicates that the ZifTox test can identify polluted ground water from a site also determined to be toxic by an independent biomonitor test as well as sophisticated EPA analyses.

Of further interest, water samples from channel 7 and pump site 39 both were inhibitory in the ZifTox test (lanes 10 and 12). Because binding inhibition was not observed at the higher TFIIIA concentrations with these particular water samples (lanes 11 and 13), the toxic agents only partially reacted with TFIIIA (approximately 50%) during the 15 minute incubation. Of note, both these water samples were toxic in the FETAX assay, ps 39 causing complete embryo lethality and channel 7 water causing 27% malformation. In conclusion, results in FIG. 2 demonstrate the usefulness of the ZifTox test in identifying a potentially harmful environmental toxic load.

The ZifTox test has several advantages over the MICROTOX, ARTOXKIT, POLYTOX, and FETAX assays. The ZifTox test uses a specific biological target (zinc finger peptides) for reactive xenobiotic chemicals whereas the biologic targets with the other tests are unknown. The ZifTox test is an in vitro assay whereas the others are in vivo assays. Most importantly, the MICROTOX, ARTOXKIT, and POLYTOX tests all assay biologic reactions (e.g. bioluminescence) which may not be biologically pertinent to higher organisms as they are performed with bacteria (MICROTOX, POLYTOX) or brine shrimp (ARTOXKIT). The FETAX test certainly monitors pollutant conditions toxic to higher organisms yet is cumbersome and time consuming to perform, traits shared by the ARTOXKIT as well. In addition, the ZifTox test monitors for bioreactivity and harm to an extremely large and important class of regulatory proteins that are only present in higher organisms.

EXAMPLE 3

Effects of Other Xenobiotic Metal Ions on the TFIIIA-5S RNA Gene Interaction

Figure 3:
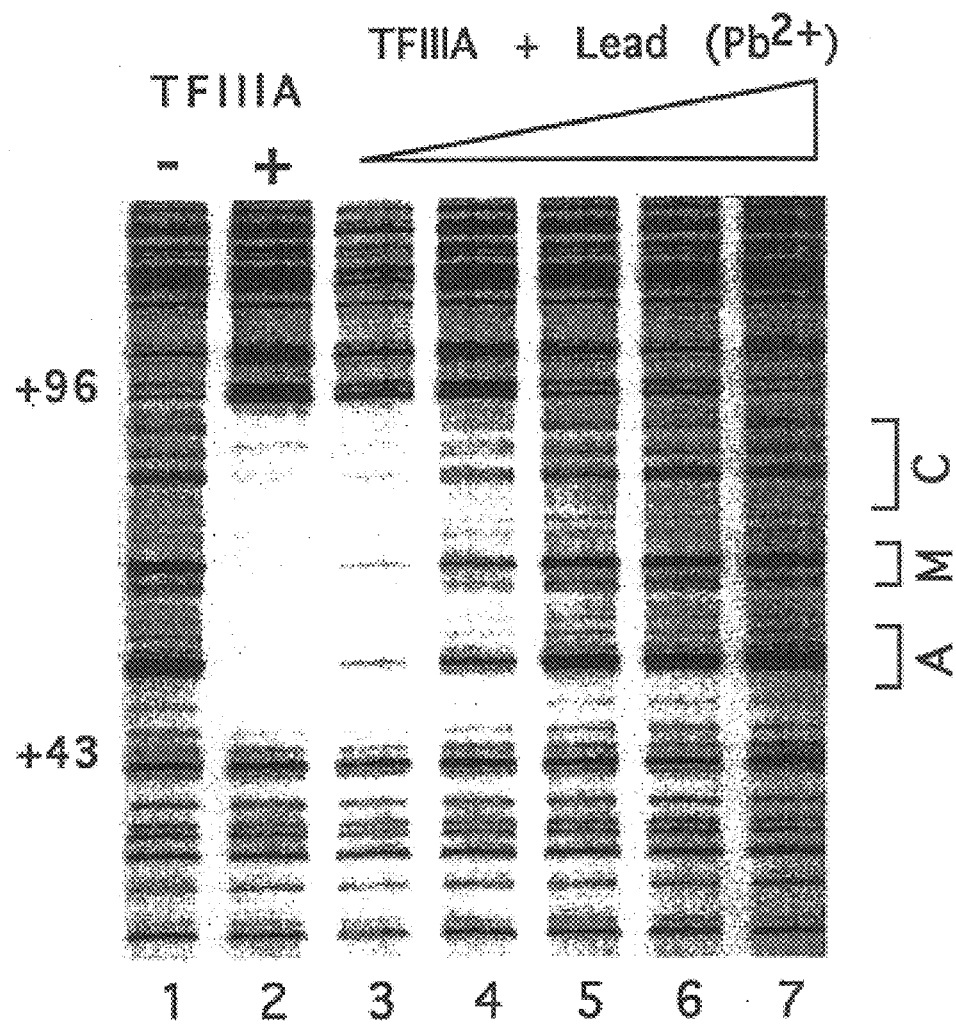
FIG. 3 is an autoradiogram of a DNase I protection assay on acrylamide-urea gel showing the effects of lead ions on the binding of TFIIIA zinc finger to the Xenopus 5S ribosomal gene.
Figure 4:
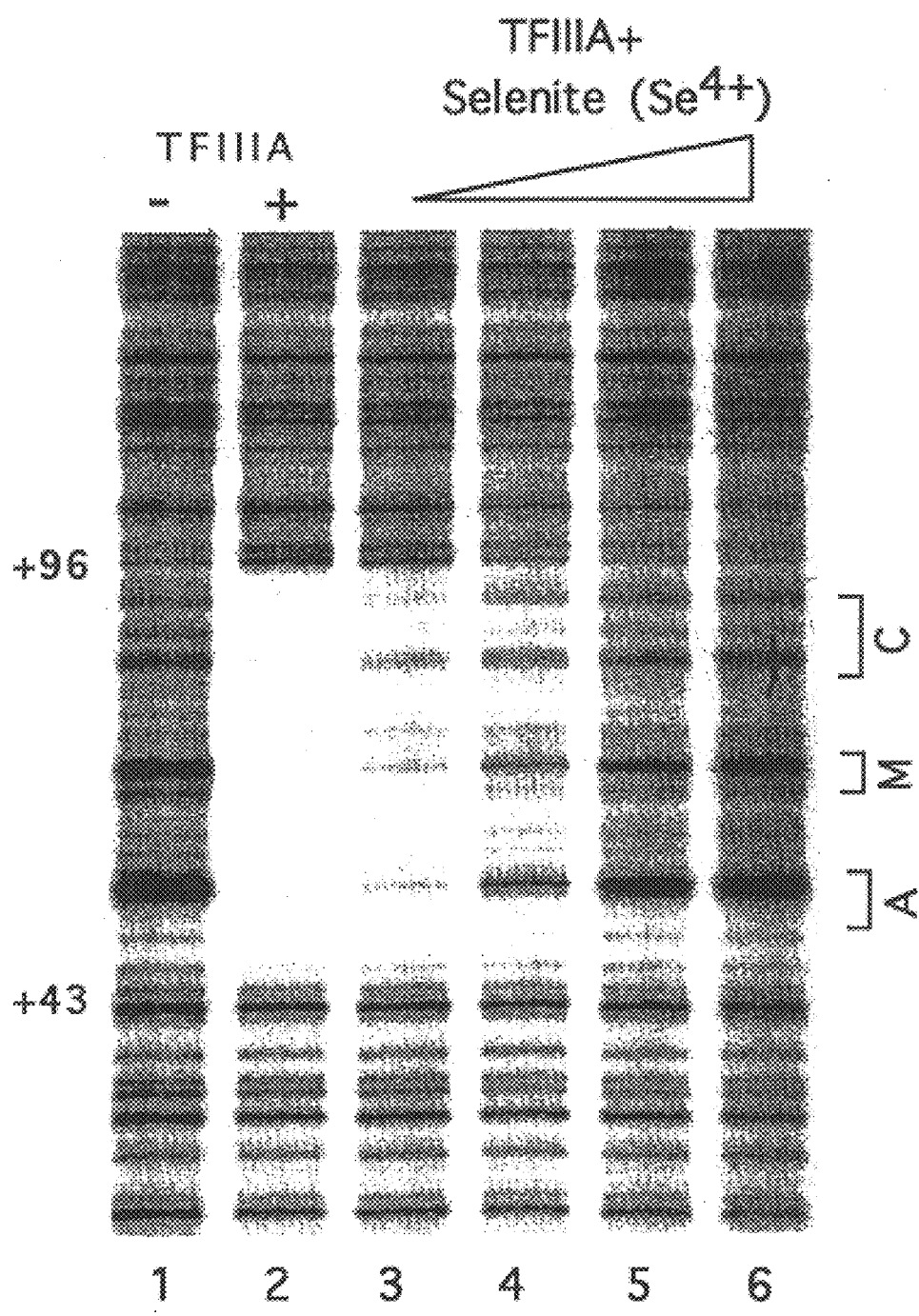
FIG. 4 is an autoradiogram of a DNase I protection assay on acrylamide-urea gel showing the effects of selenium ions on the binding of TFIIIA zinc finger to the Xenopus 5S ribosomal gene.

The effects of xenobiotic metal ions other than cadmium and aluminum which also have potentially damaging physiological effects were investigated. FIGS. 3 and 4 show that both lead ($Pb^{2+}$) and selenium ($Se^{4+}$), respectively, inhibit TFIIIA zinc finger binding to DNA as assayed by DNase I protection (using the same DNA binding assays, DNase I protection, autoradiography and DNA demarcations used for FIG. 1).

Results shown in FIG. 3 were obtained when TFIIIA used in the reactions electrophoresed in lanes 3–7 was preincubated with 5, 10, 15, 20, or 25 $\mu$M $PbCl_2$ respectively; inhibition is observed at 10 $\mu$M and higher. TFIIIA in lane 2 was not exposed to metal and the reaction in lane 1 contained radioactive DNA but no TFIIIA.

Regarding FIG. 4, TFIIIA used in the reactions electrophoresed in lanes 3–6 was preincubated with 10, 25, 50, or 100 $\mu$M $Na_2SeO_3$, respectively; inhibition is observed at 25 $\mu$M and higher. TFIIIA in lane 2 was not exposed to metal and the reaction in lane 1 contained radioactive DNA but no TFIIIA.

Figure 5:
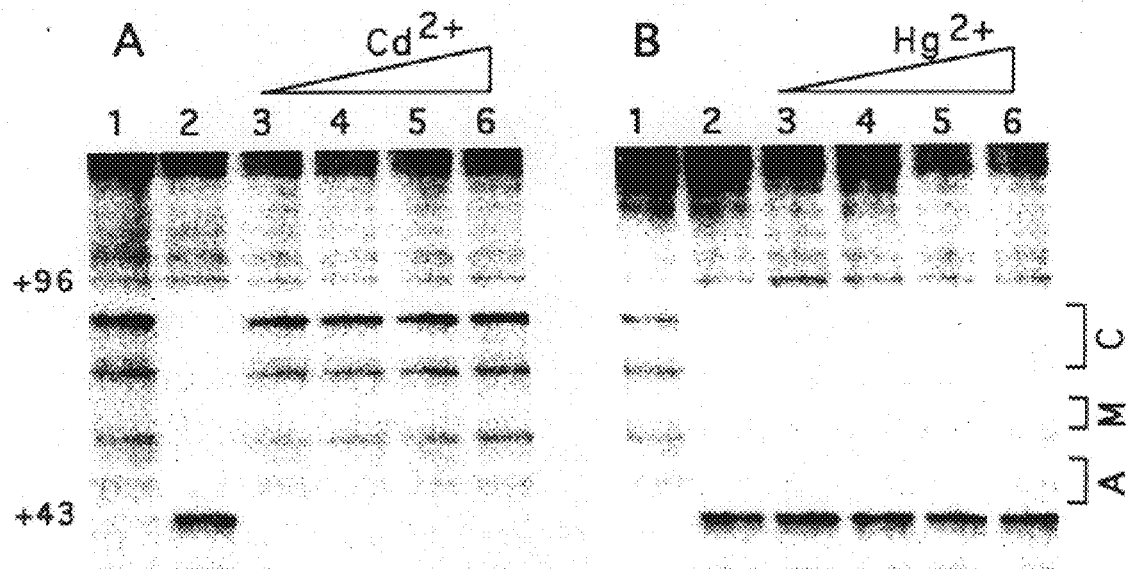
FIG. 5 is an autoradiogram of a DNase I protection assay on acrylamide-urea gel showing the effects of cadmium and mercury ions on the binding of TFIIIA zinc finger to the Xenopus 5S ribosomal gene.

Mercury, apparently, does not inhibit TFIIIA zinc finger binding to DNA as assayed by DNase I protection as shown in FIG. 5. As noted above, DNA binding assays, DNase I protection, autoradiography, and DNA demarcations are as described for FIG. 1. TFIIIA used in the reactions electrophoresed in lanes 36 was preincubated in 5, 10, 15, 20 $\mu$M $CdCl_2$ (panel A) or $HgCl_2$ respectively (panel B) ; TFIIIA in lanes 2 was not exposed to metal and the reaction in lanes 1 contained radioactive DNA but no TFIIIA.

Figure 6:
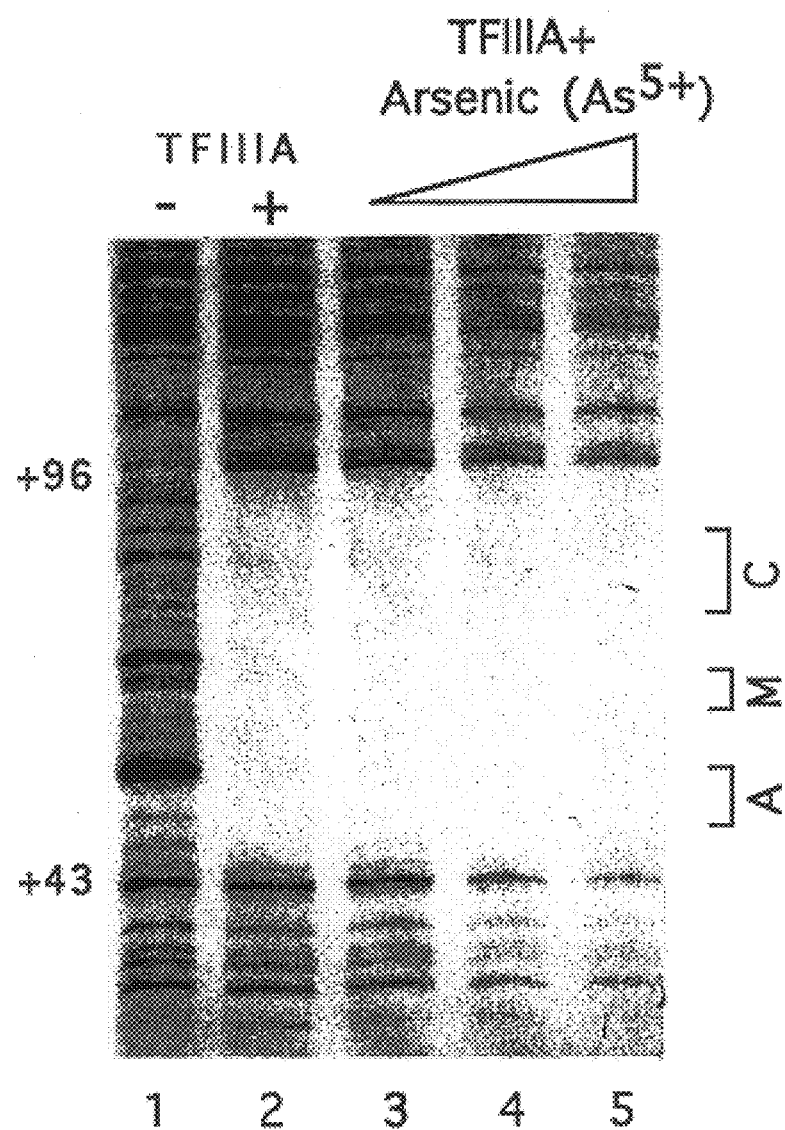
FIG. 6 is an autoradiogram of a DNase I protection assay on acrylamide-urea gel showing the effects of arsenic ions on the binding of TFIIIA zinc finger to the Xenopus 5S ribosomal gene.

Arsenic also apparently does not inhibit TFIIIA zinc finger binding to DNA as assayed by DNase I protection as shown in FIG. 6. TFIIIA used in the reactions electrophoresed in lanes 3–5 was preincubated with 0.1, 0.5, or 1.0 mM $NaH_2AsO_4$ respectively; no loss of TFIIIA-dependent protection from nucleotides +96 to +43 is observed. TFIIIA in lane 2 was not exposed to metal and the reaction in lane 1 contained radioactive DNA but no TFIIIA.

Other metal ions ($Mg^{2+}$, $Mn^{2+}$ and $Cs^{2+}$) were also found to be non-inhibitory at 10 $\mu$M concentrations (data not shown).

EXAMPLE 4

Xenobiotic Metal Ions Inhibit TFIIIA-Dependent DNA Renaturation

Besides binding to the 5S RNA gene, TFIIIA also has the ability to promote DNA renaturation and was the first transcription factor shown to possess such an activity. More recently the transcription factor/tumor suppressor p53 was also shown to promote DNA renaturation. TFIIIA renatures DNA by binding initially to complementary single-stranded DNAs, accelerating their reassociation and then remaining associated with the renatured double-stranded DNA. Unlike the DNase I protection assay of the 5S gene, TFIIIA ions retains the ability to promote DNA renaturation even when depleted of $Zn^{2+}$ ions. Because TFIIIA-dependent DNA renaturation is a DNA binding mechanism distinct from that assayed by DNase I protection, it was of interest to determine whether xenobiotic metal ions also inhibit this process.

DNA migration in the Tris-phosphate agarose gel electrophoresis system used in the DNA renaturation assay is sensitive to some types of DNA structural changes. This assay is useful in this study because it can detect structural changes in the nanomolar DNA concentration range.

Figure 7:
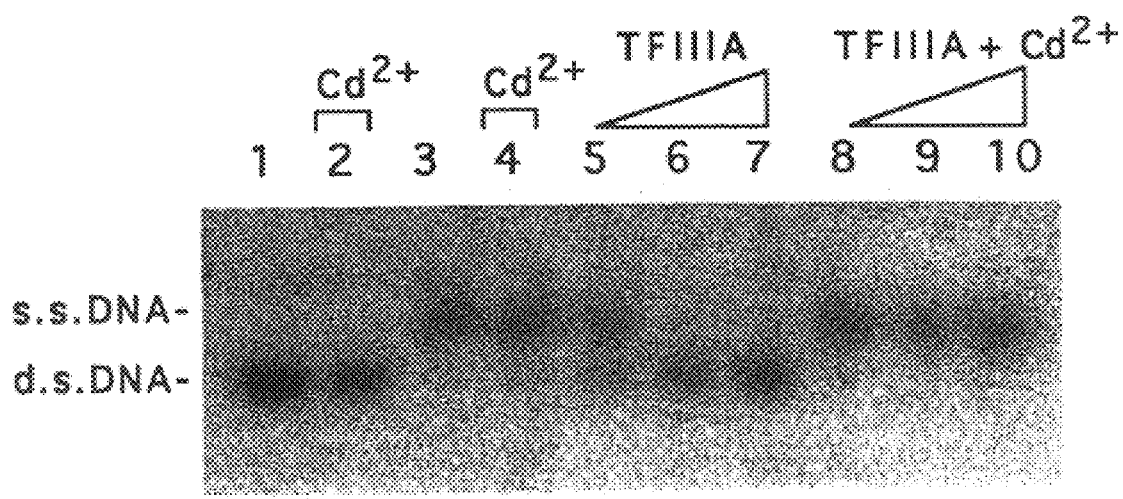
FIG. 7 is an autoradiogram of an agarose gel showing the effects of cadmium ions on the ability of the TFIIIA zinc finger to promote DNA renaturation.

Cadmium is shown in FIG. 7 to inhibit the ability of TFIIIA to promote DNA renaturation. DNA renaturation (hybridization of complementary single-stranded DNA) was assayed by binding 20 nM Xenopus TFIIIA to 2 nM heat-denatured $^{32}$P labeled 5S gene DNA for 15 min. Reactions are terminated by detergent and electrophoresed on an agarose gel which resolves the slower migrating single-stranded DNA (s.s.) from the faster migrating double-stranded DNA (d.s.) DNA bands are visualized by autoradiography. Reactions in lanes 5–7 reveal DNA renaturation (conversion of single-stranded DNA to double-stranded DNA) stimulated by increasing amounts of TFIIIA not exposed to xenobiotic metal; reactions in lanes 8–10 exhibit inhibition of DNA renaturation (no d.s. DNA formed) using increasing amounts of TFIIIA preincubated with 1 $\mu$M $CdCl_2$. Lanes 1 and 2 exhibit d.s. DNA electrophoretic migration in the absence and presence of cadmium ions; lanes 3 and 4 exhibit s.s. DNA migration in the absence and presence of cadmium.

TFIIIA isolation, $^{32}$P-end-labeling of the 5S RNA gene, denaturation and renaturation reactions, Tris-phosphate agarose gel electrophoresis and autoradiography were performed as described above in the methodology section herein. The electrophoretic migration positions of double-stranded and single-stranded 5S DNA are indicated in the left margin. Lanes 1 and 2, 1 nM double-stranded DNA incubated in the absence and presence of 1 $\mu$M $CdCl_2$ prior to electrophoresis; lanes 3 and 4, 1 nM single-stranded DNA incubated in the absence and presence of $Cd^{2+}$ ions; lanes 5–7, single-stranded DNA incubated in the presence of 10, 20 or 30 nM TFIIIA prior to electrophoresis; lanes 8–10, single-stranded DNA incubated in the presence of 1 $\mu$M $Cd^{2+}$ plus 10, 20 or 30 nM TFIIIA respectively prior to electrophoresis.

Figure 8:
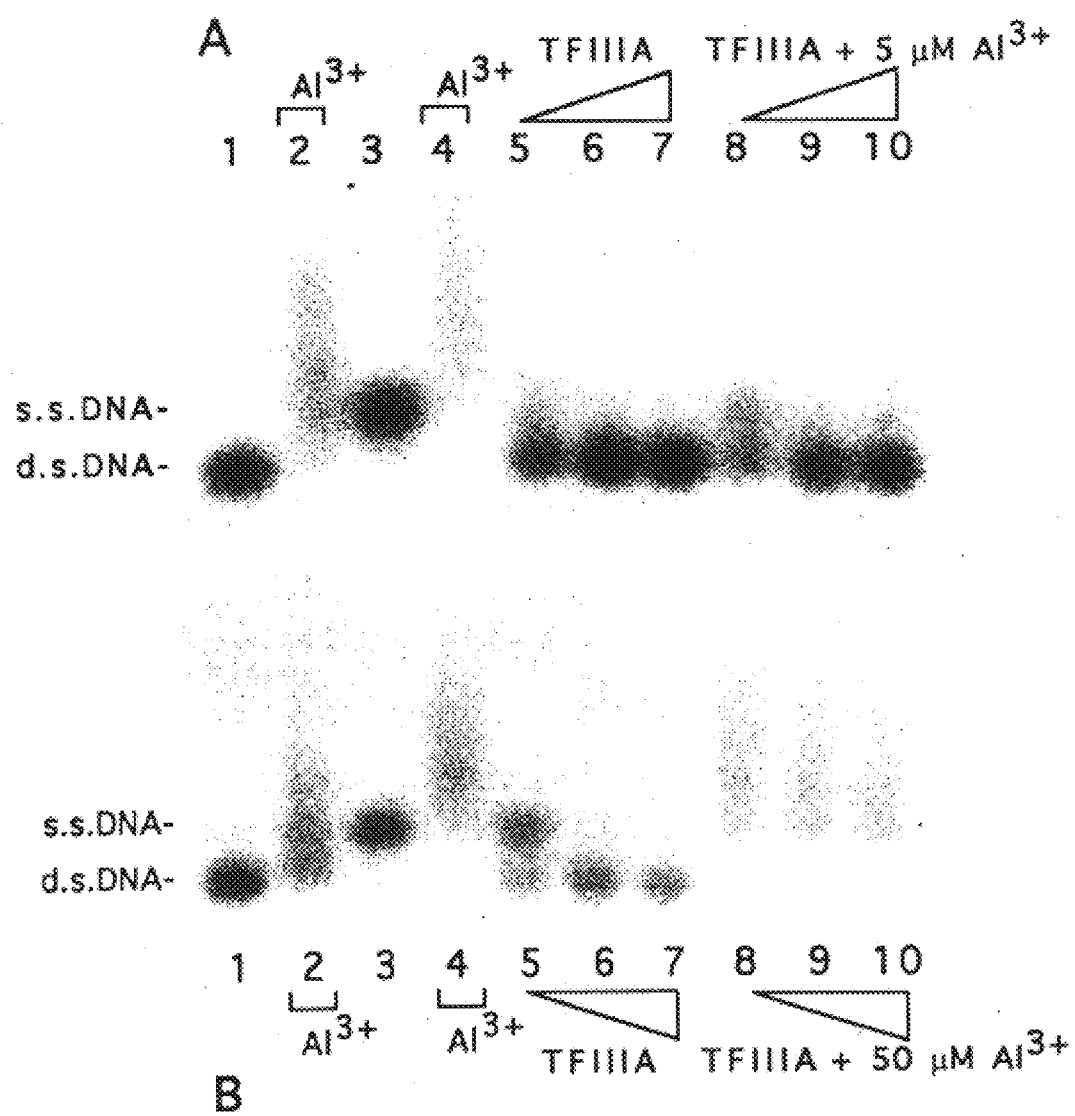
FIG. 8 is an autoradiogram of an agarose gel showing the effects of aluminum ions on the ability of the TFIIIA zinc finger to promote DNA renaturation.

As shown in FIG. 8, aluminum also inhibits TFIIIA-dependent DNA renaturation. Lanes 5–6 and 8–10 exhibit DNA renaturation in the presence of increasing concentrations of TFIIIA preincubated in the absence or presence of 5 $\mu$M $AlCl_3$ (panel A) or 50 $\mu$M $AlCl_3$ (panel B). Inhibition of TFIIIA-dependent renaturation (lack of conversion of s.s. DNA to d.s. DNA) is observed in panel B. Lanes 1 and 2 exhibit d.s. DNA electrophoretic migration in the absence and presence of aluminum ions; lanes 3 and 4 exhibit s.s. DNA migration in the absence and presence of aluminum.

Further, experiments demonstrated that $Cd^{2+}$ and, at higher concentrations, $Al^{3+}$ interact directly with TFIIIA to cause loss of DNA binding function.

The in vitro inhibitory concentration of $Cd^{2+}$ (0.1 $\mu$M) for TFIIIA is approximately 5 fold higher than the serum concentration of this ion in moderate to heavy smokers. $Cd^{2+}$ induces teratogenesis and carcinogenesis in rodents and potentially in humans as well. In vivo inhibition of specific binding of TFIIIA by $Cd^{2+}$ per se would not be expected to induce such developmental changes, because TFIIIA inhibition would shut off 5S RNA synthesis and ribosome production, which are essential for cell viability. $Cd^{2+}$ is physiologically toxic and cells contain cysteine-rich metallothionein proteins as protection (chemical "sponges") against this and other heavy metal ions. TFIIIA may be one of the biochemical targets that $Cd^2$+ inhibits in eukaryotic cells, other targets include the calcium transport machinery.

EXAMPLE 5
Change in Fluorescence with Conformational Change

Figure 9:
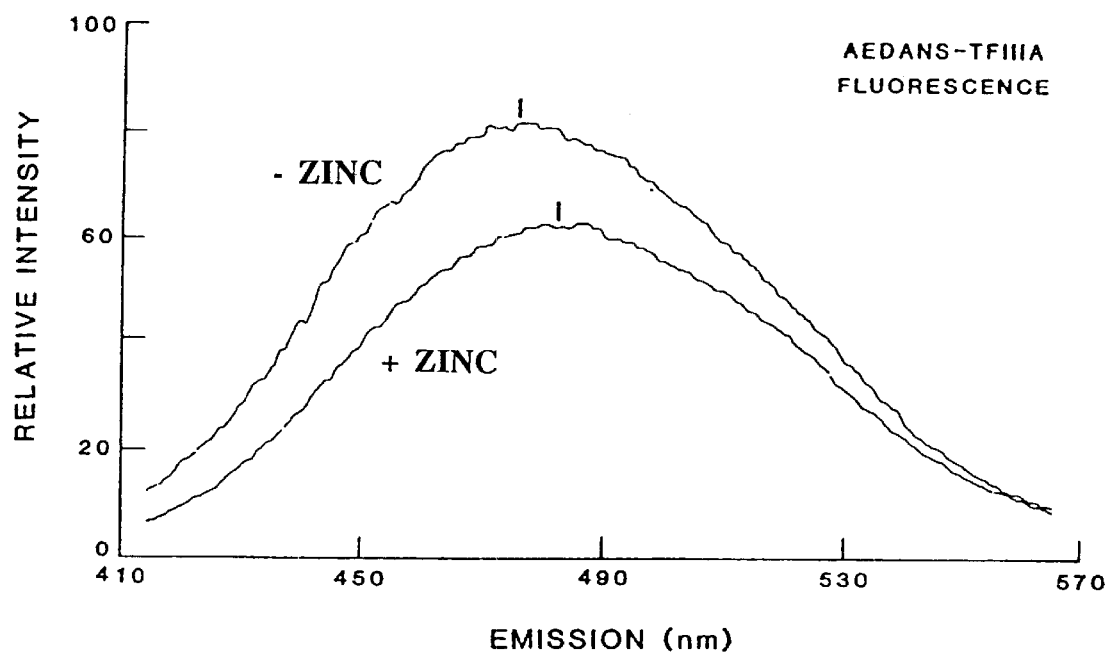
FIG. 9 is a graph showing an increase in fluorescence when a zinc finger conformational structure is altered by a xenobiotic (EDTA).

As shown in FIG. 9, zinc removal from TFIIIA zinc Fingers causes large changes in the fluorescence of a TFIIIA-bound extrinsic fluorescent probe. TFIIIA is reacted with N-iodoacetylaminoethyl-5-naphthylamine-1-sulfonic acid (I-AEDANS) under mild conditions such that TFIIIA-dependent DNase I protection of the 5S gene is not impaired. Zinc is then removed from TFIIIA (- ZINC sample) by incubation with the zinc chelator, ethylenediamine tetraacetic acid (EDTA). Relative emission fluorescent intensity spectra of the TFIIIA-bound AEDANS probe are recorded using an excitation wavelength of 360 nanometers. Removal of zinc from TFIIIA results in a 25% increase of emission fluorescence intensity as well as a blue shift in the emission wavelength from 485 nanometers to 478 nanometers.

Methodology
Isolation of 7S Particles and TFIIIA from *Xenopus laevis* Oocytes

Immature ovarian tissue was dissected from 4–5 cm female *X. laevis* frogs (Nasco, Fort Atkinson, Wis.) and homogenized briefly in 50 mM Tris-HCL, pH 7.5, 50 mM KCl, 5 mM $MgCl_2$, 0.5 mM dithiothreitol (DTT) and 0.2 mM phenylmethylsulfonyl fluoride. The homogenate was centrifuged at 10 000 g for 20 min and aliquots of the supernatant were layered on 15–30% glycerol gradients in homogenization buffer and centrifuged for 24 h at 34,000 r.p.m. in a SW41 rotor. All manipulations were performed at 0–4° C. The 7S fractions containing TFIIIA bound to 5S rRNA were identified by UV absorption of gradient fractions and further purified to 90–95% purity (judged by SDS-PAGE of 39 kDa TFIIIA) by DEAE-cellulose chromatography essentially as described in J. S. Hanas, D. J., Hazuda, D. F. Bogenhagen, F. Y. Wu and C. Wu, *J. Biol. Chem.*, 1983, 258, pp. 14120–14125. 5S RNA was removed from TFIIIA by digestion with RNase A (10 $\mu$g/ml) in 20 mM Tris-HCl, pH 7.6, 320 mM KCl, 2 mM MgCl2, 0.4 mM DTT and 0.1% NP-40 for 30 min at room temperature and then placed on ice. Protein concentration was determined by the method of Bradford using bovine serum albumin as the standard (M. M., Bradford, *Anal. Biochem.* 1976, 72, pp. 248–254).

DNase I Protection Assays

A plasmid containing the *Xenopus borealis* somatic 5S RNA gene was purified by CsCl/ethidium bromide equilibrium gradient centrifugation (J. F. Smith, J. Hawkins, R. E. Leonard, and J. S. Hanas, *Nucleic Acids Res.*, 1991, 19, pp. 6871–6876). The 303 bp DNA fragment containing the 120 bp Xenopus 5S RNA gene was end-labeled on the coding strand by digesting the plasmid first with EcoRI and incorporating [$\alpha^{32}$P] dATP with reverse transcriptase (J. F. Smith, J. Hawkins, R. E. Leonard, and J. S. Hanas, *Nucleic Acids Res.*, 1991, 19, pp. 6871–6876). The end-labeled fragment was ethanol precipitated, redigested with BamHI and the smaller fragment was purified by PAGE. Specific activity of the fragment was determined by absorbance at 260 nm and Cerenkov counting. To examine the effects of various metals on the TFIIIA-5S RNA gene interaction TFIIIA (10 nM) was incubated with the various metals (chloride salts of all metals were ultrapure grade and purchased from Aldrich; concentrations are indicated in the figure legends) in 20 mM Tris-HCl, pH 7.6, 70 mM $NH_4Cl$, 7 mM $MgCl_2$, 0.4 mM DTT and 0.1% NP-40 for 10 min prior to addition of the DNA fragment containing the end-labeled 5S RNA gene (1 nM). After addition of DNA the reaction (20 $\mu$l ) was incubated at room temperature for an additional 15 min. The reactions were then incubated for an additional 1 min in DNase I (2 $\mu$g/ml final concentration) and digestion was terminated by addition of 100 μl stop buffer (20 mM Tris-HCl, pH 7.6, 1 mM EDTA, 0.1% SDS, 30 μg/ml sonicated salmon sperm DNA). The samples were ethanol precipitated, dried, resuspended in 4 μl formamide solution (20 mM Tris-HCl, pH 7.6, 95% deionized formamide, 1 mM EDTA, 0.01% xylene cyanol and bromphenol blue), heated to 95° C. for 5 min and electrophoresed on a 7 M urea-7% polyacrylamide gel until the xylene cyanol marker had migrated two thirds the distance of the gel. Gel autoradiography was performed overnight at −70° C. with Kodak XAR-5 film and a Dupont Cronex intensifying screen.

Single-Stranded DNA Renaturation Assays

Complementary single-stranded DNA template for renaturation assays was obtained by denaturing the 303 bp $^{32}$P-end-labeled fragment (in 20 mM Tris-HCl, pH 7.6, 50 mM KCl, 1.5 mM MgCl$_2$) at 100° C. for 5 min, followed by quick cooling in an ice/water bath. The non-denatured 303 bp end-labeled fragment was used as the double-stranded DNA control. TEIIIA-dependent DNA renaturation was performed under the same TFIIIA binding conditions as described in the DNase I protection assay above. TFIIIA, DNA and metal ion concentrations are given in the figure legends. The renaturation reactions (20 μl) were quenched by addition of 4 μl electrophoresis sample buffer (20 mM Tris-HCl, pH 7.6, 10 mM EDTA, 0.5% SDS, 25% glycerol, 0.01% bromphenol blue). Agarose gel (0.6%) electrophoresis utilizing a 20 mM Tris-phosphate buffer, pH 8.3, was used to resolve single-and double-stranded DNA in the renaturation assays (R. M. Fiser-Littell and J. S. Hanas, *J. Biol. Chem.*, 1988, 263, pp. 17136–17141). Gels were exposed to Kodak XAR-5 film overnight at 4° C.

Examples of proteins comprising zinc fingers which may be used in the present invention are disclosed in the following articles, each of which is incorporated by reference herein in its entirety:

A. M. Ginsberg, B. O. King, and R. G. Roeder, "Xenopus 5S Gene Transcription Factor, TFIIIA: Characterization of a cDNA Clone and Measurement of RNA Levels Throughout Development", *Cell*, 39, pp. 474–489, (1984); C. J. Gaskins and J. S. Hanas, "Sequence Variation in Transcription Factor IIIA", *Nucleic Acids Res.*, 18, pp. 2117–2123, (1990); N. A. Woychik, and R. A. Young, "Genes Encoding Transcription Factor IIIA and the RNA Polymerase Common Subunit RPB6 are divergently transcribed in *Saccharomyces cerevisiae*", *Proc. Natl. Acad. Sci. USA*, 89, pp. 3999–4003, (1992); C. J. Gaskins, J. F. Smith, M. Olgivie and J. S. Hanas, "Comparison of the Sequence and Structure of Bur© and Rana Transcription Factor IIIA", *Gene*, 120, pp. 197–206, (1992); P. D. Drew, J. W. Nagle, R. D. Canning, K. Qzato, W. E. Biddison, and K. G. Becker, "Cloning and expression Analysis of a Human cDNA Homologous to Xenopus TFIIIA", *Gene* 159, pp. 215–218, (1995); A. J. Buckler, J. Pelletier, D. A. Haber, T. Glaser, and D. E. Housman, "Isolation Characterization, and Expression of Murine Wilms' Tumor Gene (WT1) During Kidney Development", *Mol. Cell. Biol.*, 11, pp. 1707–1712, (1991); D. Tautz, R. Lehmann, H. Schnurch, R. Schuh, E. Seifert, A. Kienlin, K. Jones and H. Jackle, "Finger Protein of Novel Structure Encoded by hunchback, a Second Member of the Gap Class of Orosophila Segmentation Genes", *Nature*, 327, pp. 383–389, (1987); K. W., Kinzler, J. M. Ruppert, S. H. Bigner, and B. Vogelstein, "The GLI Gene is a Member of the Kruppel Family of Zinc Finger Proteins", *Nature*, 332, pp. 371–374; J. T. Kadonaga, K. R. Carner, F. R. Masiarz, and R. Tjian, "Isolation of cDNA Encoding Transcription Factor Spl and Functional Analysis of the DNA Binding Domain", *Cell* 51, pp. 1079–1090, (1987); B. A. Christy, L. F. Lau, and D. Nathans, "A Gene Activated in Mouse 3T3 Cells by Serum Growth Factors Encodes a Protein with 'Zinc Finger' Sequences", *Proc. Natl. Acad. Sci. USA*, 85, pp. 7857–7861, (1988); E. Harlow, N. M. Williamson, R. Ralston, D. M. Helfman, and T. E. Adams, "Molecular Cloning and in vitro Expression of a cDNA Clone for Human Cellular Tumor Antigen p53", *Mol. Cell. Biol.*, 5, pp. 1601–1610, (1985); T. Evans, and G. Felsenfeld, "The Erythroid-Specific Transcription Factor Eryfl: A New Finger Protein", *Cell*, 58, pp. 877–885, (1989); C. D. Trainor, T. Evans, G. Felsenfeld, and M. S. Boguski, "Structure and Evolution of a Human Erythroid Transcription Factor", *Nature*, 343, pp. 92–96, (1990); S. Green, P. Walter, V. Kumar, A. Krust, J. M. Bornert, P. Argos, and P. Chambon, "Human Estrogen Receptor cDNA: Sequence, Expression and Homology to v-erb-A", *Nature*, 320, pp. 134–139, (1986); J. M. Jeltsch, Z. Krozowski, C. Quirin-Stricker, H. Gronemeyer, R. J. Simpson, J. M. Garnier, A. Krust, F. Jacob, and Chambon, P. "Cloning of the Chicken Pregesterene Receptor", *Proc. Natl. Acad. Sci USA*, 83, pp. 5424–5428, (1986); W. S. El-Deiry, T. Tokino, V. E. Velculescu, D. B. Levy, R. Parsons, J. M. Trent, D. Lin, W. E. Mercer, K. Kinzler, and B. Vogelstein, "WAF1, A Potential Mediator of p53 Tumor Suppression", *Cell* 75, pp. 817–825, (1993); and J. W. Harper, G. R. Adami, N. Wei, K. Keyomarsi, and S. J. Elledge, "The p21 cdk-Interacting Protein Cipl is a Potent Inhibitor of G1 Cyclin-Dependent Kinases", *Cell* 75, pp.805–816, (1993); Y. Miki et al., "A Strong Candidate for the Breast and Ovarian Cancer Susceptibility Gene BRCAI", *Science, Vol.* 266, 66-, (Oct. 7, 1994); Y. Cho, S. Gorina, P. Jeffrey, N. Paveletich, "Crystal Structure of a p53 Tumor Suppressor-DNA Complex: Understanding Tumorigenic Mutations", *Science*, Vol. 265, 346-, (Jul. 15, 1994); G. Mardon and D. Page, "The Sex-Determining Region of the Mouse Y Chromosome Encodes a Protein with a Highly Acidic Domain and 13 Zinc Fingers", *Cell, Vol.* 56, 765–770, (Mar. 10, 1989); V. Cunliffe, P. Koopman, A. McLaren and J. Trosdale, "A Mouse Zinc Finger Gene Which is Transiently Expressed During Spermatogenesis", *The Embo Journal*, Vol. 9, No. 1, 197–205, (1990); V. Seyfert, N. Sukhatme, and J. Monroe, "Differential Expression of a Zinc Finger-Encoding Gene in Response to Positive Versus Negative Signaling Through Receptor Immunoglobulin in Murine B Lymphocytes", *Molecular and Cellular Biology*, 2083–2088, (May 1989); K. Moses, M. Ellis, and G. Rubin, "The Glass Gene Encodes a Zinc-Finger Protein Required by Drosophila Photoreceptor Cells", *Nature*, Vol. 340, 531-, (Aug. 17, 1990); L-H. Wang, S. Tsai, R. Cook, W. Beattie, M-J. Tsai, and B. O'Malley, "COUP Transcription Factor is a Member of the Steroid Receptor Superfamily", *Nature*, Vol. 340, 163-, (Jul. 13, 1989); A. Prats, L. Sarih, C. Gabus, S. Litvak, G. Keith, and J. Darlix, "Small Finger Protein of Avian and Murine Retroviruses Has Nucleic Acid Annealing Activity and Positions the Replication Primer tRNA onto Genomic RNA", *The EMBO Journal*, Vol. 7, No. 6, 1777–1783, (1988); K. Morishita, D. Parker, M. Mucenski, N. Jenkins, N. Copeland and J. Ihle, "Retroviral Activation of a Novel Gene Encoding a Zinc Finger Protein in IL-3-Dependent Myeloid Leukemia Cell Lines:, *Cell.* Vol. 54, 831–840, (Sept. 9, 1988); C-M. Fan and T. Maniatis, "A DNA-Binding Protein Containing Two Widely Separated Zinc Finger Motifs That Recognize the Same DNA Sequence", *Genes & Development*, 4:29–42, (1990), C. Passananti, A. Felsani, M. Caruso and P. Amati, "Mouse Genes Coding For 'Zinc-Finger'-Containing Proteins: Characterization and Expression in Differentiation Cells", *Proc. Natl. Acad. Sci. USA*, Vol. 86, 9417–9421, (December 1989); A. Isaac, M. Sargent, and J. Cooke, "Control of Vertebrate Left-Right Asymmetry by a Snail-Related Zinc Finger Gene", *Science,* Vol. 275, 1301–1304, (Feb. 28, 1997).

The present invention further contemplates synthetic zinc fingers which are not found in naturally-occurring proteins but which have properties which are similar to naturally-occurring proteins zinc fingers as defined herein. The present invention contemplates using such synthetic zinc fingers in methods and kits for testing for analytes as described elsewhere herein. Examples of synthetic zinc Linger designs are disclosed in J. Nardelli, T. J., Gibson, C. Vesque, and P. Charnay, "Base Sequence Discrimination by Zinc-Finger DNA-Binding Domains", *Nature,* 349, pp. 175–178, (1991); and J. R. Desjarlais, and J. M. Berg, "Use of a Zinc-Finger consensus Sequence Framework and Specificity Rules to Design Specific DNA Binding Proteins", *Proc. Natl. Acad. Sci. USA,* 90, pp. 2256–2260, (1993), which are hereby incorporated by reference herein in their entirety.

Shown below in Examples 6–12 are several methods which can be used in accordance with the present invention. It will be appreciated by a person of ordinary skill in the art that the invention contemplated herein is not limited to the methods described herein or to the exact steps described in the examples herein. These examples are merely illustrative of the various methods and kits which can be used in the practice of the present invention.

EXAMPLE 6

Enzyme-Linked Substrate Assay

The present invention in one embodiment contemplates a xenobiotic assay method and kit using one or more zinc fingers in an enzyme-linked substrate assay (FIG. 10). In the assay a solution or suspension 10 of enzyme-bound zinc finger is provided. The solution 10 may comprise one or more different zinc ringers. The enzyme linked to the zinc fingers is any one of those well known to those of ordinary skill in the art which are used in such enzyme linked substrate assays. A test sample 12 which is being analyzed for content or presence of one or more xenobiotic elements or compounds is provided. The zinc finger solution 10 and the test sample 12 are combined and mixed to form a mixture 14. Into the mixture 14 is inserted a test strip 16 (or the test strip 16 is otherwise treated with the sample mixture 14, or the sample mixture 14 is otherwise applied to the test strip 16 in any acceptable manner). The test strip 16 (which may be any suitable support surface such as paper, glass, or plastic) has applied thereto one or more nucleic acid, peptide or protein binding templates 18 to which the specific zinc fingers used herein can preferentially bind when the zinc finger is in its native conformational structure. Examples of such zinc fingers, as noted above, are zinc fingers from proteins such as those in the TFIIIA class, human tumor suppressor protein p53, GATA1, cdk inhibitor protein p21, BRCA 1 and the steroid hormone receptor superfamily. The test strip 16 is incubated within the mixture 14 for a surficient time to allow unaltered or less affected zinc fingers to bind in the mixture 14 to their corresponding templates 18 and 18a. Xenobiotics in the mixture 14 which react with the zinc fingers therein will inhibit or reduce the ability of the affected zinc fingers (i .e., zinc fingers affected by one or more xenobiotics within the mixture 14) to bind to their corresponding templates 18 and 18a by altering the conformational structure of the zinc fingers.

After the incubation period the test strip 16 is rinsed in any acceptable manner known to one of ordinary skill in the art to remove zinc fingers which are not bound to a template 18 or 18a. The test strip 16 is then introduced into a solution 20 of a substrate for the enzyme bound to the zinc finger. As will be understood by those of ordinary skill in the art, the substrate is a compound which when acted upon by the enzyme is converted into a product having some measurable characteristic such as a color change. After the test strip 16 is incubated in the substrate solution 20 it is removed therefrom and the templates 18 or 18a on the test strip 16 are compared to standards and the change in binding affinity represented by the measurable characteristic is measured or detected. For example, the measurable characteristic may be a color change which can be compared with color charts 22 and 22a for comparing with templates 18 and 18a, respectively. These results are then interpreted as to the presence of xenobiotics in the test sample 10. Less binding represents the presence of xenobiotics in the test sample 10, for example.

EXAMPLE 7

Fluorescent Zinc Finger Assay

The present invention in an alternative embodiment contemplates a xenobiotic assay method and kit using a fluorescence assay (FIG. 11). In the assay a solution or suspension 26 of a zinc finger-fluorescent label complex is provided. The solution 26 may comprise one or more different zinc finger complexes, each comprising a zinc finger and a fluorescent label. The fluorescent label linked to the zinc finger (or zinc fingers) is any one of those labels which are well known to those of ordinary skill in the art and which are used in such fluorescent assays. A test sample 28 which is being analyzed for content or presence of one or more xenobiotics is provided. The zinc finger solution 26 and the test sample 28 are combined and mixed to form a mixture 30. Into the mixture 30 is inserted a test strip 32 (or the test strip is otherwise treated as noted above). The test strip 32 has applied thereto one or more nucleic acid, peptide or protein binding templates 34 and 34a to which the specific zinc fingers can preferentially bind when the zinc finger is in its native conformational structure. The test strip 32 is incubated within the mixture 30 to allow unaltered or less affected zinc fingers in the mixture 30 to bind to their corresponding templates 34 or 34a. Xenobiotics in the mixture 30 which react with the zinc fingers will inhibit or reduce the ability of the affected zinc fingers to bind to their corresponding templates 34 or 34a by altering the conformational structure of the zinc fingers.

After the incubation period the test strip 32 is rinsed to remove zinc fingers which are not bound to a template 34 or 34a. The test strip 32 is then irradiated with an excitation wavelength 36, in a manner known to those of ordinary skill in the art. The portions of the template 34 or 34a to which the fluorescent label is attached via unaffected zinc fingers will emit a fluorescent emission wavelength which is detected and/or measured in a manner known in the art. The fluorescence emission from the templates 34 and 34a on the test strip 32 are compared to standards to assess the degree of change in binding affinity (conformational change) in the zinc fingers. The results are then interpreted as to the presence of xenobiotics in the test sample 28.

EXAMPLE 8

Enzyme-Linked Antibody Assay

Figure 12:
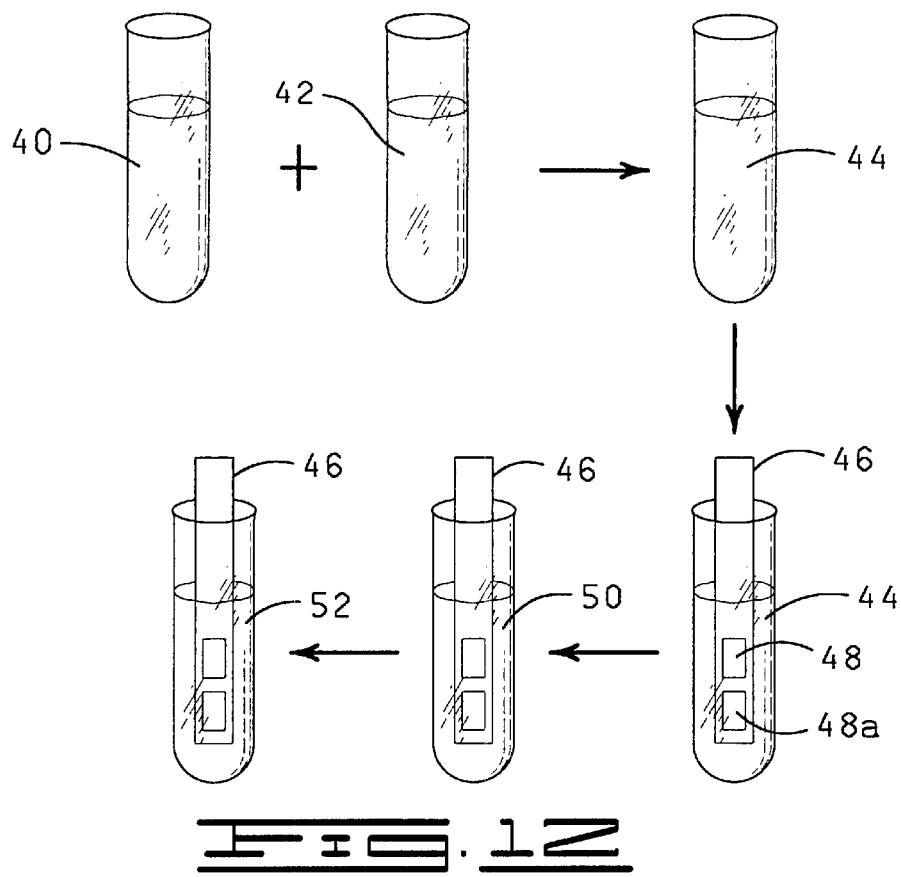
FIG. 12 is a schematic of an enzyme-linked antibody assay for use in the present invention.

The present invention in another embodiment contemplates a xenobiotic assay method and kit using one or more zinc fingers in an enzyme-linked antibody assay (FIG. 12). in the assay a solution or suspension 40 of one or more types of zinc finger is provided. A test sample 42 which is being analyzed for content or presence of one or more xenobiotics is provided. The zinc finger solution 40 and the test sample 42 are combined and mixed to form a mixture 44. Into the mixture 44 is inserted a test strip 46 (as treated as above). The test strip 46 (as described above) has applied thereto one or more binding templates 48 and 48a to which the specific zinc fingers in the mixture 44 can preferentially bind when the zinc finger is in its native conformational structure. The test strip 46 is incubated within the mixture 44 to allow unaltered or less affected zinc fingers to bind to their corresponding templates 48 or 48a. Xenobiotics in the mixture which react with the zinc fingers will inhibit or reduce the ability of the affected zinc fingers to bind to their corresponding templates 48 or 48a as explained above.

After the incubation period the test strip 46 is rinsed to remove zinc fingers which are not bound to a template 48 or 48a. The test strip 46 is then introduced into a solution 50 containing enzyme-linked antibodies which specifically bind to the zinc finger which bound to the template 48 or 48a. Following this, the test strip 46 (having antibodies bound to the template-bound zinc finger) is then introduced into a solution 52 of a substrate for the enzyme. As will be understood by those of ordinary skill in the art, the substrate in solution 52 is a compound which when acted upon by the enzyme is converted into a product having some measurable characteristic such as a color change. After the test strip 46 is incubated in the substrate solution 52 it is removed and the templates 48 and 48a on the test strip 46 are compared to standards and the change in color, or other characteristic, is measured or detected and is related to the presence or absence of one or more xenobiotics in the test sample 40.

EXAMPLE 9
DNase I Protection Assay

Figure 13:
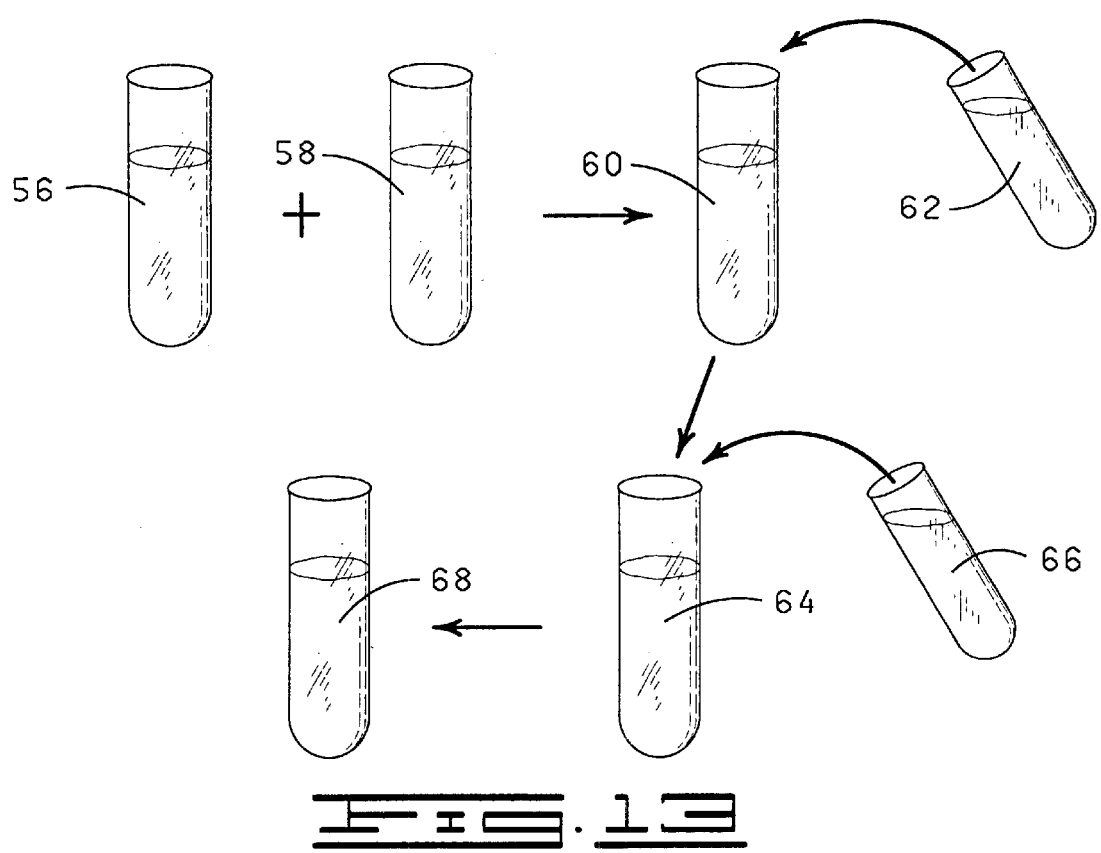
FIG. 13 is a schematic of a DNase I protection assay for use in the present invention.

The present invention in this embodiment contemplates a xenobiotic assay method and kit using one or more zinc fingers in a DNase I protection assay (FIG. 13). In the assay a solution or suspension 56 of zinc finger is provided. The solution 56 may comprise one or more different zinc fingers. A test sample 58 which is being analyzed for content or presence of xenobiotics is provided. The zinc finger solution 56 and the test sample 58 are combined and mixed to form a mixture 60. Combined with the mixture 60 is a suspension 62 of one or more nucleic acid templates (as described above) to which the specific zinc fingers can preferentially bind when the zinc finger is in its native conformational structure. Examples of such zinc fingers are described above. The combined mixture 64 is incubated to allow unaltered zinc fingers to bind to their corresponding templates from the suspension 62. Xenobiotics in the mixture which react with the zinc fingers will inhibit the ability of the affected zinc fingers to bind to their corresponding nucleic acid templates.

After the incubation period a cleavage enzyme 66 (such as DNase I) is added to the reaction mixture 64 to form an enzyme mixture 68 wherein DNA not protected by zinc fingers is cleaved into smaller nucleic acid fragments. As will be understood by those of ordinary skill in the art, the resulting DNA fragments in the mixture 68 are then characterized by an analysis method such as gel electrophoresis. The distribution of the fragments is then analyzed and compared to standards for relating to the presence or amount of xenobiotics in the test sample 56. One of ordinary skill in the art will appreciate that when templates comprising peptides proteins or RNA are used, other appropriate cleavage enzymes will be used.

EXAMPLE 10
Simple Fluorescence Assay

Figure 14:
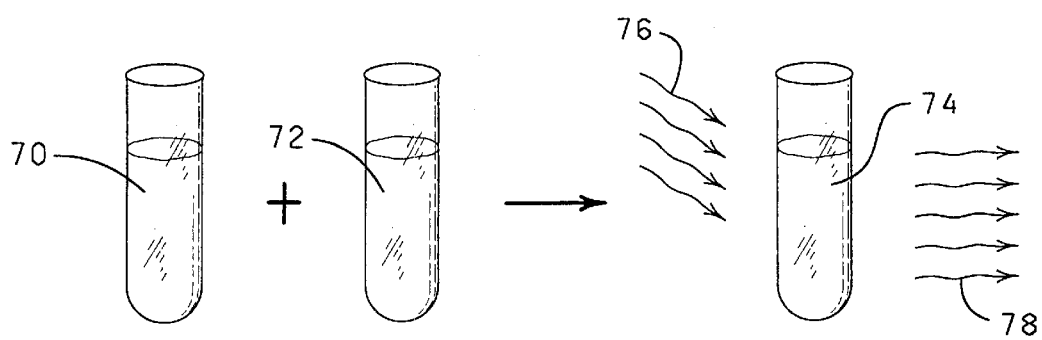
FIG. 14 is a schematic of a simple fluorescence assay for use in the present invention.

The present invention in one embodiment contemplates a xenobiotic assay method and kit using one or more zinc fingers in simple fluorescence assay (FIG. 14). In the simple fluorescence assay a solution or suspension 70 of a complex comprising a zinc finger linked to a moiety such as I-AEDANS is provided. The solution 70 may comprise one or more different zinc fingers, as noted above. As shown here the chemical group or fluorescent label linked to the zinc finger is I-AEDANS but may be any chemical group or fluorescent label well known to those of ordinary skill in the art which is known to change in fluorescence intensity when the base molecule to which it is attached (e.g., the zinc finger) is conformationally altered. A test sample 72 which is being analyzed for content or presence of one or more xenobiotics is provided. The zinc finger solution 70 and the test sample 72 are combined and mixed to form a mixture 74. The mixture 74 is incubated to allow xenobiotics therein to react with the zinc finger-I-AEDANS complex.

After the incubation period the reaction mixture 74 is illuminated with an excitation wavelength 76, and the intensity of the resulting fluorescent emission 78 from the mixture 74 is measured. When the conformational structure of the zinc finger is altered, for example, by a xenobiotic present in the mixture, the intensity of the emission wavelength 78 increases. The increase in intensity of emission 78 is related to the presence and amount of a xenobiotic in the test sample 70.

EXAMPLE 11
DNA Renaturation Assay

Figure 15:
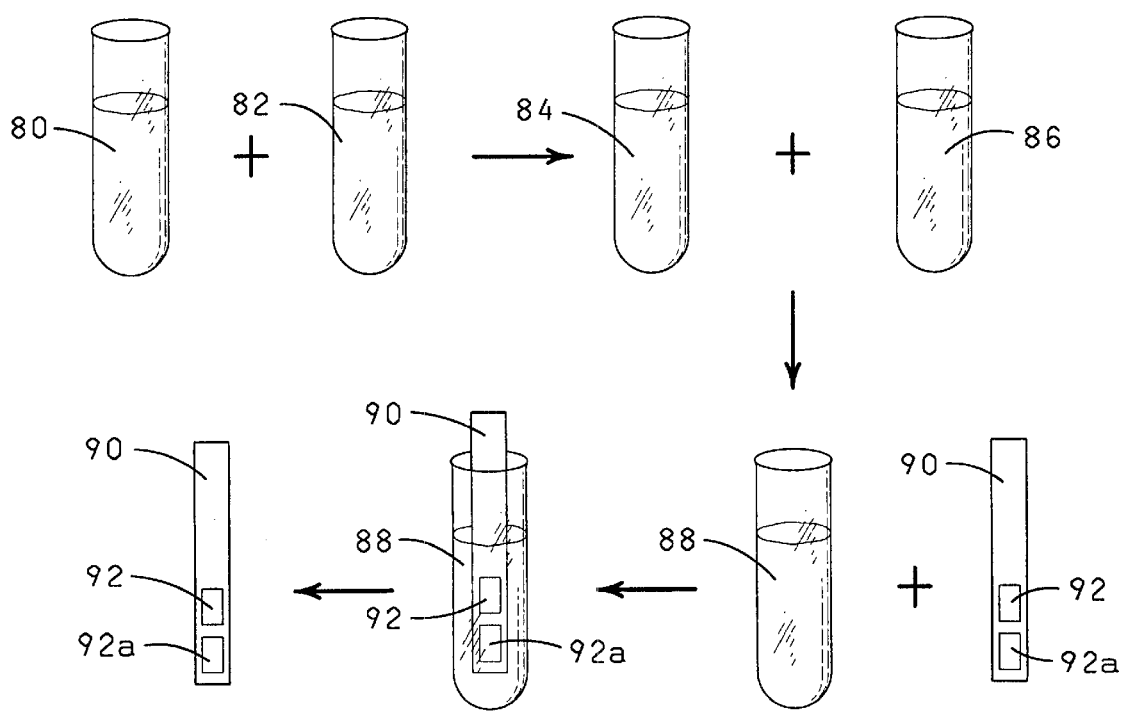
FIG. 15 is a schematic of a DNA renaturation assay for use in the present invention.

The present invention in another embodiment contemplates a xenobiotic assay method and kit using one or more zinc fingers in a renaturation assay (FIG. 15). In the assay a solution or suspension 80 of one or more types of zinc fingers is provided. A test sample 82 which is being analyzed for content or presence of one or more xenobiotics is provided. The zinc finger solution 80 and the test sample 82 are combined and mixed to form a mixture 84. Added to the mixture 84 is one or more types of single stranded DNA 86 (ssDNA) to which the zinc fingers in the mixture 84 can bind forming a ssDNA-zinc finger mixture 88. Into the mixture 88 is inserted a test strip 90 (or the test strip is otherwise treated as described previously). The test strip 90 has applied thereto one or more single stranded nucleic acid binding templates 92 or 92a which are complementary to the ssDNA in the mixture 88 and to which the specific zinc fingers in the mixture 88 can preferentially bind when the zinc finger is in its native corformational structure. Examples of such zinc fingers have been noted above. The ssDNA in the mixture 88 may be labeled with a fluorescent label or may be modified with a chemically modified nucleotide serving as a ligand for an enzyme or an affinity label such as biotin-streptavidin plus an enzyme. In an alternative version of this embodiment (not shown), the test strip 90 is incubated within the zinc finger-test sample mixture 84 prior to exposure to the ssDNA solution 86 to allow unaltered or less affected zinc fingers to bind to their corresponding ssDNA templates on the test strip 90. Xenobiotics in the mixture 84 which react with the zinc fingers will inhibit the ability of the zinc fingers to bind to their corresponding templates 92 and 92a by altering the conformation of the zinc fingers. Alternatively, the ssDNA solution 86 and zinc finger mixture 84 may be mixed to form mixture 88 and incubated prior to its exposure to the test strip 90, as shown in FIG. 15.

After the incubation period the test strip 90 is removed from the mixture 88 and is rinsed to remove zinc fingers or ssDNA which are not bound to a template 92 or 92a. The test strip 90 may then be introduced into a solution of a substrate for the enzyme if the zinc finger is enzyme linked. Alternatively, the templates 92 and 92a are irradiated to measure fluorescence, or renaturation is measured in any other way known to those of ordinary skill in the art. As discussed above, Zinc fingers promote renaturation of complementary nucleic acid fragments to which the zinc fingers specifically blind. Xenobiotics which induce conformational changes in zinc fingers will inhibit the promotional effect of the zinc fingers on the nucleic acid renaturation process. Therefore, the effect on the renaturation can be related to the presence or amount of xenobiotics in the test sample 80.

EXAMPLE 12
Gel Shift Assay

The present invention in this embodiment contemplates a xenobiotic assay method and kit using one or more zinc fingers in a gel shift assay (FIG. 16). In the assay a solution or suspension 96 of zinc finger is provided. The solution 96 may comprise one or more different zinc fingers. One or more test samples, for example, 98a, 98b, and 98c which are being analyzed for content or presence of xenobiotics are provided. A portion of the zinc finger solution 96 is combined and mixed with each of the test samples 98a–98c to form mixtures 100a–100c, respectively. Combined with a portion of the solution 96 for use as a control and with each mixture 100a–100c is a suspension 102 of one or more zinc finger binding templates forming mixtures 104–104c, respectively. The specific zinc fingers can preferentially bind to the templates when the zinc finger is in its native conformational structure. Examples of such zinc fingers have been noted above. The mixtures 104–104c are incubated to allow unaltered zinc fingers to bind to their corresponding nucleic acid templates. Xenobiotics in the mixtures 104a–104c which react with the zinc fingers will inhibit the ability of the zinc fingers to bind to their corresponding nucleic acid templates. Mixture 104 serves as a control.

After the incubation period the zinc finger-test sample-nucleic acid template mixtures 104a–104c and mixture 104 are applied to a polyacrylamide gel 106 (or other suitable substrate) to which electric current is applied. Nucleic acid templates which are not protected by zinc fingers (e.g., lanes A and B) will migrate further on the gel 106 than nucleic acid fragments which have the zinc fingers bound thereto (control and "C" lane). As will be understood by those of ordinary skill in the art, the distribution of the bands on the gel are then analyzed and compared to standards for relating to the presence and amounts of xenobiotics in the test sample 96. Mixtures comprising xenobiotics will be characterized by longer migration distances.

Changes may be made in the construction and the operation of the various components, elements and Kits described herein or in the steps or the sequence of steps of the methods described herein without departing from the spirit and scope of the invention as defined in the following claims.

What is claimed is:

1. A kit for testing an environmental sample, comprising:
at least one native zinc finger having a zinc atom coordinated therein and having a characteristic native conformational structure, the native zinc finger having a binding affinity for a template; and
a quantity of the template, the template being selected from the group consisting of DNA, RNA and protein.

2. The kit of claim 1 wherein said native zinc finger has a fluorescent label attached thereto.

3. The kit of claim 1 further comprising a quantity of an enzyme-linked antibody for combining with said native zinc finger.

4. The kit of claim 3 further comprising a quantity of a substrate for reacting with the enzyme linked to the antibody.

5. The kit of claim 1 wherein said native zinc finger has an enzyme linked thereto.

6. The kit of claim 1 further comprising a quantity of at least one enzyme for fragmenting said template for further analysis.

7. The kit of claim 1 wherein said native zinc finger is derived from a protein selected from the group consisting of the TFIIIA superfamily, human tumor suppressor protein p53, GATA1, cdk inhibitor protein p21, BRCA 1, and the steroid hormone receptor family.

8. The kit of claim 1 wherein said template is disposed on a support surface.

* * * * *

UNITED STATES PATENT AND TRADEMARK OFFICE
CERTIFICATE OF CORRECTION

PATENT NO.    : 6,451,618 B2
DATED         : September 17, 2002
INVENTOR(S)   : Jay S. Hanas It is certified that error appears in the above-identified patent and that said Letters Patent is hereby corrected as shown below:

Title page,
Item [56], References Cited, OTHER PUBLICATIONS, "Kang et al." reference "Researc" should read -- Research --.

Column 9,
Line 11, "Inhibited" should be -- inhibited --.
Line 66, "birds" should be -- binds --.

Column 10,
Line 11, should read as follows:

-- The DNase I protection assay of Xenopus TFIIIA binding to the Xenopus 5S ribosomal gene was performed by first binding 20 nM Xenopus TFIIIA (reacted with metals described below) with 2 nM 32p end-labeled 5S DNA in a 20 •1 reaction volume for 15 min. DNase I is then added to a final concentration of 1 •g/ml for 1 min to nick the DNA. The digested DNA in the reactions is ethanol precipitated and electrophoresed on an acrylamide-urea gel. Visualization of DNA bands in the TFIIIA binding site (nucleotides + 96 to +43) is accomplished by autoradiography. The presence of bands in this site indicates lack of TFIIIA binding whereas the absence of bands in this site indicates binding.
Panel A: TFIIIA used in DNA binding reactions electrophoresed in lanes 2-6 was preincubated in 0.05, 0.01, 0.1, 0.5, or 1.0 •M cadmium and higher. TFIIIA in lane 1 was not exposed to metal. Letters C. M, and A in the left margin demarcate the C-box, intermediate element, and A-box of TFIIIA binding site from nucleotides +96 to +43 on the 5S gene internal control region (panel B). Panel B: TFIIIA used in lanes 3-8 was preincubated in 1, 3, 5, 7, 9, or 12 •M aluminum (AlCl3) respectively; inhibition of binding is observed at 3 •M and higher. TFIIIA in lane 2 was not exposed to metal and the reaction in lane 1 contained radioactive DNA but no TFIIIA. --

UNITED STATES PATENT AND TRADEMARK OFFICE
CERTIFICATE OF CORRECTION

PATENT NO.    : 6,451,618 B2
DATED         : September 17, 2002
INVENTOR(S)   : Jay S. Hanas It is certified that error appears in the above-identified patent and that said Letters Patent is hereby corrected as shown below:

Column 16,
Line 30, delete "-," after number "66".
Line 33, delete "-," after number "346".
Line 48, delete "-," after number "531".
Line 51, delete "-," after number "163".

Signed and Sealed this

Ninth Day of March, 2004

JON W. DUDAS
*Acting Director of the United States Patent and Trademark Office*